US007470779B2

(12) United States Patent
Boyle et al.

(10) Patent No.: US 7,470,779 B2
(45) Date of Patent: Dec. 30, 2008

(54) PROCESS FOR DECREASING AGGREGATE LEVELS OF PEGYLATED PROTEIN

(75) Inventors: Denis M. Boyle, Marthasville, MO (US); John J. Buckley, Ofallon, MO (US); Gary V. Johnson, St. Charles, MO (US); David E. Steinmeyer, Clarkson Valley, MO (US); Michele Toal, Chesterfield, MO (US); Serdar Aykent, Chesterfield, MO (US); Anurag S. Rathore, Thousand Oaks, CA (US)

(73) Assignee: Pfizer Inc., New York, NY (US)

( * ) Notice: Subject to any disclaimer, the term of this patent is extended or adjusted under 35 U.S.C. 154(b) by 107 days.

(21) Appl. No.: 10/665,361

(22) Filed: Sep. 22, 2003

(65) Prior Publication Data
US 2005/0085631 A1  Apr. 21, 2005

Related U.S. Application Data

(60) Provisional application No. 60/412,227, filed on Sep. 20, 2002.

(51) Int. Cl.
*C07K 14/00* (2006.01)
(52) U.S. Cl. .......................................... 530/416; 514/2
(58) Field of Classification Search ........................ None
See application file for complete search history.

(56) References Cited

U.S. PATENT DOCUMENTS

| 5,149,647 A | * | 9/1992 | Burling ...................... 435/192 |
| 5,153,265 A | | 10/1992 | Shadle et al. ................ 525/54.1 |
| 5,290,685 A | * | 3/1994 | Koide et al. ................. 435/68.1 |
| 5,849,535 A | | 12/1998 | Cunningham et al. | |
| 5,969,109 A | * | 10/1999 | Bona et al. ................ 530/387.3 |
| 6,057,292 A | | 5/2000 | Cunningham et al. | |
| 6,096,870 A | * | 8/2000 | Mozaffar et al. ............ 530/366 |
| 2002/0037841 A1 | * | 3/2002 | Papadimitriou ................. 514/8 |
| 2003/0171285 A1 | * | 9/2003 | Finn et al. ...................... 514/12 |

FOREIGN PATENT DOCUMENTS

| WO | WO 96/02570 | 2/1996 |
| WO | WO 96 40731 | 12/1996 |
| WO | WO 02/057478 A1 | 7/2002 |

OTHER PUBLICATIONS

Olson et al., "Chapter 12: Preparation and Characterization of Poly-(ethylene glycol)ylated Human Growth Hormone Antagonist", pp. 170-181, Poly(ethylene glycol): chemistry and biological applications, J. Milton Harris, editor, Samuel Zalipsky, editor, (1997).*
Pharmacia Fine Chemicals, "Chapter 2: Ion Exchange Chromatography, principles and methods", (1980).*
Andersson et al., "Isolation and characterization of a trisulfide variant of recombinant human growth hormone formed during expression in *Escherichia coli*," Int. J. Peptide Protein Res. 47:311-321 (1996).
J. Houk and G.M. Whitesides, "Structure-Reactivity Relations for Thiol-Disulfide Interchange," J. M. Chem. Soc., 109:6825-6836 (1987).
A. Jesperson et al., "Characterisation of a trisulphide derivative of biosynthetic human growth hormone produced in *Escherichia coli*," Eur. J. Biochem. 219:365-373 (1994).
Jorgensen et al., "Quantifying biosynthetic human growth hormone in *Escherichia coli* with electrophoresis under hydrophobic conditions," J. Chromatography A 817:205-214 (1998).
The Merck Index, 12th Edition, S. Budavari (Editor), Merck & Co., Inc., Therapeutic Category and Biological Activity Index, p. THER-19 (under "Chelating Agent"), Whitehouse Station, NJ (1996).

* cited by examiner

*Primary Examiner*—Anand U Desai
(74) *Attorney, Agent, or Firm*—Gregg C. Benson; Nicholas I. Slepchuk

(57) ABSTRACT

The present invention is directed generally to recombinant methods for making a desired pegylated protein and pooling of same. The method(s) yield a polypeptide product containing reduced levels of aggregate thereof pooled to provide the desired pegylated isoforms thereof.

28 Claims, 4 Drawing Sheets

B-2036

(Trisulfide Isoform Impurity of B-2036)

```
                         SEQUENCE LISTING

<160> NUMBER OF SEQ ID NOS: 2

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80
```

-continued

```
Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Lys Ile Gln Thr Leu Met Gly Arg Leu
                115                 120                 125

Glu Asp Gly Ser Pro Arg Thr Gly Gln Ile Phe Lys Gln Thr Tyr Ser
                130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                    165                 170                 175

Leu Arg Thr Val Gln Cys Arg Ser Val Glu Gly Ser Cys Gly Phe
                180                 185                 190

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
                35                  40                  45

Gln Thr Ser Leu Cys Phe Ser Glu Ser Ile Pro Thr Pro Ser Asn Arg
            50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
                115                 120                 125

Glu Asp Gly Ser Pro Arg Thr Gly Gln Ile Phe Lys Gln Thr Tyr Ser
                130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                    165                 170                 175

Leu Arg Ile Val Gln Cys Arg Ser Val Glu Gly Ser Cys Gly Phe
                180                 185                 190
```

PROCESS FOR DECREASING AGGREGATE LEVELS OF PEGYLATED PROTEIN

CROSS-REFERENCE TO RELATED APPLICATION

This application is a non-provisional application claiming priority to its corresponding provisional application No. 60/412,227, filed Sep. 20, 2002. This application is a continuation-in-part of non-provisional U.S. application Ser. No. 10/662,884, filed Sep. 16, 2003. Both the above-noted provisional and non-provisional applications are incorporated herein by reference in their entirety.

FIELD OF THE INVENTION

The present invention is directed generally to recombinant methods for making a desired pegylated polypeptide. These method(s) yield a pegylated polypeptide product containing reduced levels of aggregate and/or certain isoform impurities thereof. In particular, the present invention is also directed to (1) a recombinant method for preparing growth hormone with decreased aggregate and/or isoform impurities thereof and (2) a recombinant method for preparing a growth hormone antagonist (e.g., such as pegvisomant, and its protein intermediate) with decreased aggregate and/or isoform impurities thereof. More specifically, the isoform impurities that are decreased by methods of the present invention are the trisulfide and des-phe isoform impurities of growth hormone and growth hormone antagonist (or its intermediate), respectively. Also, the aggregate is the undesirable aggregate of pegylated growth hormone, pegylated growth hormone antagonist, or a pegylated protein, in general.

BACKGROUND OF THE INVENTION

Pegvisomant (Somavert®; Pharmacia Corp.) is a human growth hormone receptor antagonist. It is an analog of human growth hormone ("hGH") that has been structurally altered. The amino acid sequence of the protein component/intermediate (B-2036) of pegvisomant differs from the amino acid sequence of hGH at nine positions. The specific amino acid substitutions are as follows: H18D, H21N, G120K, R167N, K168A, D171S, K172R, E174S, and 1179T. As is well recognized in the art, the first letter (i.e., H18D) represents the amino acid in the sequence of hGH at the numbered position (i.e., $18^{th}$ amino acid position as indicated by H18D) which is substituted with the amino acid designated by the second letter (i.e., H18D). Therefore, H18D designates a substitution of the amino acid his by the amino acid asp at the $18^{th}$ amino acid position of the wild-type hGH amino acid sequence.

FIG. 1A schematically shows the amino acid sequence structure of the protein component/intermediate (B-2036) of pegvisomant (PEG B-2036 or B-2036 PEG) with asterisks indicating the potential sites of polyethylene glycol polymer ("PEG" unit) attachment. Additionally, the amino acid sequence listing of the protein component/intermediate (B-2036-without PEG unit attachment) of pegvisomant is identified herein as SEQ. ID. NO. 1. For comparison, the amino acid sequence listing of human growth hormone is identified herein as SEQ. ID. NO. 2. Both sequence listings are provided herewith. See also Jorgensen et al., "Quantifying biosynthetic human growth hormone in *Escherichia coli* with electrophoresis under hydrophobic conditions," J. Chromatography A 817:205-214 (1998) for the sequence of hGH.

Structurally, pegvisomant is a protein (containing 191 amino acid residues) to which predominantly 4 to 6 PEG units are covalently bound. The molecular weight of the protein component/intermediate (B-2036) of pegvisomant is 21,998 Daltons. The molecular weight of each PEG unit of pegvisomant is approximately 5000 Daltons. Thereby the predominant molecular weights of pegvisomant are approximately 42,000 (4 PEG units/molecule), 47,000 (5 PEG units/molecule) and 52,000 (6 PEG units/molecule) Daltons.

Referring to the agonist, and without being bound by theory, it is believed that endogenous hGH activates its receptors when a single hGH molecule binds to two of its adjacent (and identical) receptor molecules, inducing hormone-mediated receptor homodimerization. See U.S. Pat. Nos. 5,849,535 and 6,057,292. The activity of hGH depends on its ability to bind two of its adjacent (and identical) receptors across two separate binding sites (site 1 and site 2) on the same hGH molecule. These hGH binding sites, designated as site 1 and site 2, are numbered 1 and 2 to reflect the order of their binding to two adjacent (and identical) hGH receptors which mediate hGH-dependent homodimerization.

Further, without being bound by theory, it is believed that pegvisomant selectively binds to human growth hormone receptors ("GH receptors") on cell surfaces, where it blocks the binding of endogenous human growth hormone, thereby interfering with human growth hormone signal transduction. The structural modifications to the protein portion (also called "component" or "intermediate") of pegvisomant (relative to hGH) allow pegvisomant to competitively block interaction between an hGH molecule and an hGH receptor. Pegvisomant binds to the GH receptor, therefore, blocking GH binding since the receptor is occupied. The structural modifications prevent receptor dimerization, as a result signal transduction does not occur. By so blocking the required close interaction between an hGH molecule and an hGH receptor, pegvisomant blocks the hGH-mediated homodimerization of the hGH receptors, giving pegvisomant its antagonist activity.

This antagonist is used to treat conditions, including, but not limited to, acromegaly in patients who do not adequately respond to surgery, radiation therapy, and/or other conventional medical therapies, or who cannot otherwise tolerate these therapies. In addition, the structural modifications to the protein portion (B-2036) of pegvisomant cause it to exhibit a binding affinity for the prolactin receptor which is lower than that of hGH, thereby minimizing the undesirable lactation-related side effects associated with the use of pegvisomant.

The protein intermediate portion (B-2036) of pegvisomant is synthesized by a strain of *Escherichia coli* bacteria that has been genetically modified by the addition of a plasmid that carries a gene for the growth hormone receptor antagonist (B-2036). B-2036 is then recovered from the microbial cells and purified. The purified B-2036 is then pegylated to produce pegvisomant (PEG B-2036). U.S. Pat. Nos. 5,849,535 and 6,057,292 describe methods of making B-2036 and methods for conjugating one or more PEG units to B-2036, albeit without details as to how to decrease, reduce, eliminate, reverse and/or prevent the formation of unacceptably high levels of the trisulfide and des-phe isoform impurities thereof.

One of the problems encountered using conventional recombinant manufacturing methods to make B-2036 is the formation of its isoform impurities, such as its des-phe and the trisulfide isoforms. Another of the problems encountered using conventional manufacturing and purification methods to make B-2036 PEG (i.e., pegylated B-2036 such as pegvisomant) from B-2036 is the formation of an undesirable "aggregate" of B-2036 PEG as further discussed below.

The des-phe isoform impurity is one wherein the B-2036 molecule is missing its amino-terminal phenylalanine. See FIG. 1A depicting the subject amino-terminal phenylalanine residue (i.e., indicated by the letter "F") adjacent the —NH$_2$ end of B-2036. The trisulfide isoform impurity is one wherein the B-2036 molecule contains an extra sulfur atom that forms a "trisulfide bridge" within the molecule. See box in FIG. 1B. Also, see Andersson et al., "Isolation and characterization of a trisulfide variant of recombinant human growth hormone formed during expression in *Escherichia coli*," Int. J. Peptide Protein Res. 47:311-321 (1996) and A. Jesperson et al., "Characterisation of a trisulphide derivative of biosynthetic human growth hormone produced in *Escherichia coli*," Eur. J. Biochem. 219:365-373 (1994). Without being bound by theory, it is believed that these isoform impurities typically are generated during cell growth (e.g., fermentation) and expression (synthesis and secretion) of B-2036 in genetically modified host cells, and/or during extraction and purification of the B-2036 protein.

Regarding the problem with the "aggregate," formation of such "aggregate" leads to a decreased yield of the desired protein and to an increased cost of producing the same. Also, if the "aggregate" level is too high, the final protein may be of such low purity that it becomes unsuitable for therapeutic use.

Regarding certain impurities, International Application WO 94/24157 (published Oct. 27, 1994) discloses a hydrophobic derivative of hGH comprising an extra sulfur atom as compared to the native hGH. See WO 94/24157 at page 3, lines 3-10. The extra sulfur atom of the hydrophobic derivative of hGH forms a "trisulfide bridge" yielding an hGH trisulfide variant. See WO 94/24157 at page 7, lines 11-16. The WO 94/24157 reference further states that this hGH trisulfide variant can be converted back to its native hGH form by treating the hGH trisulfide variant with a mercapto compound such as cysteine, glutathione, 2-mercapto ethanol or dithiothreitol. See WO 94/24157 at pages 4 and 5.

International Application WO 96/02570 (published Feb. 1, 1996) describes another method for converting the hGH trisulfide variant back to its native form using either sodium sulfite, potassium sulfite, ammonium sulfite, or an alkaline-earth metal sulfite such as magnesium sulfite or calcium sulfite. See WO 94/24157 at page 4, lines 17-21.

International Application WO 00/02900 (published Jan. 20, 2000) entitled "Method for the production of recombinant peptides with a low amount of trisulfides" discusses "a method for the reduction of the amount of trisulfides in the production of recombinant peptides, e.g., both proteins and smaller peptides. The invention is based on the novel and unexpected finding that the amount of trisulfides in the production of recombinant peptides could be reduced by the addition of a metal salt, preferably in excess, already during or after fermentation and not, as earlier suggested, by conversion of the formed trisulfides of growth hormone into the native form." See WO 00/02900 at page 2, lines 21-27. The WO 00/02900 reference further states "[t]he protein can be any recombinant protein but is preferably recombinant growth hormone which can be both human and animal such as human growth hormone (hGH), bovine growth hormone (bGH) and porcine growth hormone (pGH)." See WO 00/02900 at page 3, lines 4-6.

International Application No. WO 02/057478 (published Jul. 25, 2002) entitled "Methods and Composition For Extracting Proteins From Cells" is directed to a method of releasing a protein from a host cell by contacting the host cell with a reducing agent and a detergent. The reference states that the purpose of the reducing agent is to "facilitate[ ] the recovery of proteins in their native conformations." See WO 02/057478 at page 2, lines 16-18. Furthermore, WO 02/057478 describes that the "one or more reducing agents are agents . . . that reduce disulfide bonds and/or maintain sulfhydryl residues in the[ir] reduced form. Any such reducing agent or agents may be used. In a preferred embodiment, the one or more reducing agents used are selected from the group consisting of, dithiothrietol (DTT); dithioerythritol (DTE); Cysteine (Cys) and Tris 2-carboxyethyphosphine (TCEP)." See WO 02/057478 from page 3, line 24 to page 4, line 4.

For other references regarding purification see U.S. Pat. No. 6,265,542 B1 (Fahrner et al. entitled "Purification of Molecules"); U.S. Pat. No. 6,333,398 B1 (Blank entitled "Protein Purification"); U.S. Pat. No. 5,747,639 (Seely entitled "Use of Hydrophobic Interaction Chromatography to Purify Polyethylene Glycols"); International Application No. PCT/US96/19459 (Ibrahim et al. entitled "Activated Linkers and Methods for Making and Purifying the Same"); and U.S. Patent Application No. U.S. 2002/002271 A1 (Rinderknecht et al. entitled "Antibody Purification").

The above-noted references, however, are silent with regard to the prevention, reversal, reduction, or elimination of isoform impurity formation associated with a growth hormone antagonist such as pegvisomant or its protein portion, B-2036 and/or aggregate formation of pegylated protein, e.g., pegvisomant. Accordingly, there is a need for improved methods of making B-2036 that decrease, attenuate, prevent, minimize, reverse and/or eliminate the formation of its isoform impurities (trisulfide and/or des-phe) and/or aggregate formation of pegylated protein. Likewise, these references also are silent as to the detection, attenuation, minimization, reversal, reduction or elimination of the formation of the des-phe isoform impurity of growth hormone and/or aggregate formation of pegylated protein, e.g., pegylated growth hormone or pegylated human growth hormone. Accordingly, there is a need for improved methods of making growth hormone that decrease, attenuate, prevent, minimize, reverse and/or eliminate the formation of its des-phe isoform impurity and/or aggregate formation of pegylated protein, e.g., pegylated growth hormone or pegylated human growth hormone.

SUMMARY OF THE INVENTION

Figure 1A:
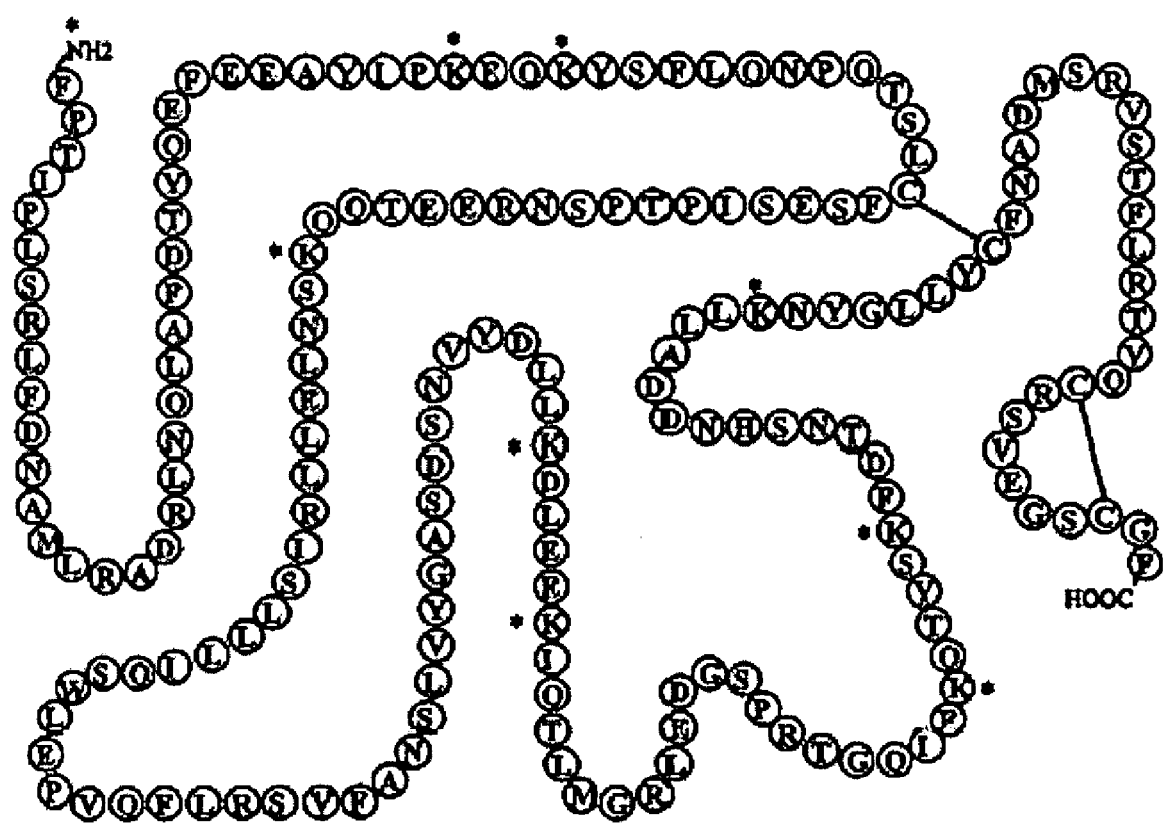
FIG. 1A depicts the amino acid sequence of B-2036 which corresponds to SEQ. ID. NO. 1. The asterisks (*) in FIG. 1A indicate nine (9) potential sites for covalent attachment of PEG units to each molecule of B-2036. Note that while nine (9) possible sites are identified, not all 9 sites have to be covalently bound to PEG units. Preferably, there are 4-6 PEG units per B-2036 molecule.

In view of the foregoing need to provide an improved process for making a recombinant pegylated polypeptide growth hormone agonist, a recombinant pegylated polypeptide human growth hormone agonist, a recombinant pegylated polypeptide growth hormone antagonist, and/or a recombinant pegylated polypeptide human growth hormone antagonist, with decreased levels of undesirable aggregate and/or isoform impurities thereof, the present invention is directed to improved processes for producing recombinant pegylated polypeptide growth hormone (including, but not limited to, human growth hormone) and recombinant pegylated polypeptide growth hormone antagonist (including, but not limited to, human growth hormone antagonist) with decreased levels of their aggregate, des-phe and/or trisulfide isoform impurities.

With regard to recombinant growth hormone (including, but not limited to hGH), formation of its des-phe isoform impurity is decreased by sufficient addition of (1) a chelating agent or (2) a metal salt, respectively.

With regard to recombinant growth hormone antagonist (including, but not limited to, human growth hormone antagonist), its trisulfide isoform impurity is decreased by sufficient contact between the trisulfide isoform impurity and (1) a mercapto compound, (2) a chelating agent, (3) a metal salt, (4) a mercapto compound together with a metal salt, or (5) a mercapto compound after contact with a chelating agent but in the absence of the chelating agent, respectively.

With regard to recombinant growth hormone antagonist (including, but not limited to, human growth hormone antagonist), formation of its des-phe isoform impurity is decreased by addition of (1) a chelating agent or (2) a metal salt, respectively.

With regard to a recombinant pegylated protein (including, but not limited to, pegylated hormone, pegylated growth hormone antagonist, pegylated human growth hormone antagonist, pegylated growth hormone and/or pegylated human growth hormone), the level of aggregate is maintained or decreased at or below a desirable level by anion exchange chromatography during separation of pegylated isoforms thereof.

DETAILED DESCRIPTION OF THE PREFERRED EMBODIMENTS

The following abbreviations are used in this application.
AC affinity chromatography
AEX anion exchange
API active pharmaceutical ingredient
BI Bulk intermediate; B-2036 (no pegylation)
B-2036 PEG pegylated B-2036
PEG B-2036 pegylated B-2036
CE capillary electrophoresis
CEX cation exchange
cm centimeter
CV column volume
DEAE diethylaminoethyl
HEPES N-(2-hydroxyethyl)piperazine N-(2-ethane)sulfononic acid
HIC hydrophopic interaction chromatography
IEX ion exchange
kDa kiloDaltons
L liters
LPM liters per minute
mL or ml milliliter
mM milliMolar
mS milliSiemen
MWCO molecular weight cutoff
μm micrometer
N Normality
NaCl sodium chloride
NaOH sodium hydroxide
NWP normalized water permeability
PEG polyethylene glycol molecule or variant thereof
PEG-1 one molecule of B-2036 pegylated with 1 molecule of PEG or variant thereof
PEG-2 one molecule of B-2036 pegylated with 2 molecule of PEG or variant thereof
PEG-3 one molecule of B-2036 pegylated with 3 molecule of PEG or variant thereof
PEG-4 one molecule of B-2036 pegylated with 4 molecule of PEG or variant thereof
PEG-5 one molecule of B-2036 pegylated with 5 molecule of PEG or variant thereof
PEG-6 one molecule of B-2036 pegylated with 6 molecule of PEG or variant thereof
PEG-7 one molecule of B-2036 pegylated with 7 molecule of PEG or variant thereof
PEG-8 one molecule of B-2036 pegylated with 8 molecule of PEG or variant thereof
PEG-9 one molecule of B-2036 pegylated with 9 molecule of PEG or variant thereof
RPHPLC reversed phase high performance liquid chromatography
SD standard deviation
SDS-PAGE sodium dodecyl sulfate polyacrylamide gel electrophoresis
SEHPLC size exclusion high performance liquid chromatography
TMP trans membrane performance
TRIS tris-(2-hydroxymethyl)aminomethane
UF/DF ultrafiltration/diafiltration
UV ultraviolet
WFI water for injection The term "pegylated protein" includes, but is not limited to, a hormone, growth hormone, human growth hormone, growth hormone antagonist, human growth hormone antagonist, an antibody (or fragments thereof), and B-2036 PEG. "Pegylated protein" also includes, but is not limited to, one or more proteins of interest pegylated at one or more sites.

Unless indicated otherwise, the term "aggregate" refers to a spaghetti-like clump of one or more proteins of interest, whether pegylated or unpegylated. An "aggregate" is a multiplicity of protein molecules that have become grouped through steric interaction or otherwise with one another. Examples of "aggregate" include, but are not limited to, entangling between (1) a multiplicity of pegylated protein molecules, (2) a multiplicity of unpegylated protein molecules, and/or (3) at least one pegylated protein molecule and at least one unpegylated protein molecule.

Unless indicated otherwise, "unpegylated protein impurity" includes, but is not limited to, unpegylated proteins i.e., proteins without an attached PEG molecule or variant thereof.

Unless indicated otherwise, "stoichiometric weight ratio" refers to the amount of free PEG molecules to the amount of unpegylated protein molecules of interest.

Unless indicated otherwise, the term "pegylated protein isoform(s)" refers to a protein of interest having one or more PEG moieties attached thereto, preferably by covalent attachment. For example, the term "PEG-1" refers to B-2036 having one PEG molecule attached thereto, preferably at a position such as a lysine amino acid residue and/or the amino terminus. Likewise, PEG-2, PEG-3, PEG-4, PEG-5, PEG-6, PEG-7, PEG-8, and PEG-9 refer to the number of PEG molecules attached to one molecule of B-2036. Thus, PEG-2 refers to one B-2036 having two PEG molecules attached thereto and PEG-3 refers to three molecules of PEG attached to one molecule of B-2036 and so forth.

Unless indicated otherwise, the term "packed bed volume" refers to a packed bed volume of a particular resin packed according to manufacturer's suggested operating conditions Unless indicated otherwise, the term "isoform impurity" refers to at least the trisulfide isoform impurity, or the des-phe isoform impurity described herein. The term "isoform impurity" may also include other impurities recognized in the art.

The term "CE pooling conductivity" refers to the conductivity measurement of the collected CV fraction being subjected to CE.

The terms "growth hormone antagonist" and "growth hormone receptor antagonist" include (but are not limited to) pegylated polypeptides and polypeptides that inhibit or otherwise antagonize the binding of growth hormone to its growth hormone receptor to block the biological effect(s) of growth hormone. Preferably, the pegylated "growth hormone antagonist" or the pegylated "growth hormone receptor antagonist" is pegylated B-2036, B-2036, or a variant thereof. "Variants" include, but are not limited to, homologues (particularly homologues with conservative amino acid substitutions, additions or deletions relative to B-2036), analogues, fragments, pseudopeptides, antibodies, etc. thereof (respectively) having growth hormone receptor antagonist activity.

The terms "growth hormone agonist" and "growth hormone receptor agonist" include (but are not limited to) pegylated polypeptides and polypeptides that bind to and activate its growth hormone receptor. Preferably, the "growth hormone agonist" or the "growth hormone receptor agonist" is pegylated human growth hormone, human growth hormone or a variant thereof. "Variants" include, but are not limited to, homologues (particularly homologues with conservative amino acid substitutions, additions or deletions relative to human growth hormone), analogues, fragments, pseudopeptides, antibodies, etc. (respectively) having growth hormone receptor agonist activity.

The term "and" may mean "and" or "or" as appropriate or necessary to recite a process to yield the desired decrease in the level of the relevant impurity (e.g., trisulfide or des-phe isoform impurity and/or aggegate).

The term "or" may mean "and" or "or" as appropriate or necessary to recite a process to yield the desired decrease in the level of the relevant impurity (e.g., trisulfide or des-phe isoform impurity and/or aggegate).

As used herein, unless indicated otherwise, the term "decrease" (or apparent variations thereof) means to maintain, eliminate, minimize, reduce, prevent, reverse and/or attenuate the amount of the "aggregate" level of the pegylated protein of interest and/or the relevant isoform impurity, whether it be the trisulfide isoform impurity or the des-phe isoform impurity.

Unless indicated otherwise, the term "host cell" (or apparent variations thereof) refers to any host cell in which recombinant B-2036 or recombinant hGH may be formed. Accordingly, the host cell may be a mammalian host cell, a plant host cell, or a microbial host cell such as $E.\ coli$. or even yeast cells. It is important to note that the host cell be one that is sufficient to grow the desired recombinant B-2036 protein component or recombinant hGH therein. As such, there is no limitation as to what the host cell may be except that it be one capable of recombinantly producing the B-2036 protein component or recombinant hGH of interest or "variants" thereof.

Furthermore, as used herein, unless otherwise indicated, the term "growing" (or apparent variations thereof, e.g., growth) includes, but is not limited to, fermenting and culturing, or otherwise causing the host cell(s) to proliferate sufficiently to produce desired amounts of the recombinant B-2036 protein component or recombinant hGH.

Further, while the present invention is described with respect to recombinant B-2036, and recombinant B-2036 PEG, unless indicated otherwise, it is understood that the subject invention may be used with any recombinant growth hormone agonist, recombinant growth hormone antagonist, whether it be mammalian growth hormone or its antagonist, human growth hormone or its antagonist, or bovine growth hormone or its antagonist, etc.

Pegvisomant (referenced herein either as PEG B-2036 or B-2036 PEG) is the pegylated form of recombinant protein (B-2036) produced in recombinant host cells (e.g., recombinant, genetically modified $E.\ coli$. host cells). The B-2036 protein is produced during cell growth (e.g., by fermentation) and expression (synthesis and secretion). After its production, B-2036 is isolated (e.g., by homogenization) followed by purification (e.g., by extraction, centrifugation, reverse phase and anion-exchange chromatography, and buffer exchange). However, as noted during recombinant production of the B-2036 protein, undesirable isoform impurities of B-2036 are formed, which are the trisulfide and the des-phe isoform impurities of B-2036.

As noted, FIG. 1A illustrates the amino acid sequence of B-2036 with the standard 1-letter abbreviations indicating which amino acid is present at each lettered position. For reference, see Table 1 below indicating the correspondence between the letter and its associated amino acid.

TABLE 1

| Polypeptide Amino Acid |
|---|
| Ala (A) |
| Glu (E) |
| Gln (Q) |
| Asp (D) |
| Asn (N) |
| Leu (L) |
| Gly (G) |
| Lys (K) |
| Ser (S) |
| Val (V) |
| Arg (R) |
| Thr (T) |
| Pro (P) |
| Ile (I) |
| Met (M) |
| Phe (F) |
| Tyr (Y) |
| Cys (C) |
| Trp (W) |
| His (H) |

Additionally, the amino acid sequence of B-2036 is provided herein as SEQ. ID. NO. 1 and the amino acid sequence hGH is provided herein as SEQ. ID. NO. 2.

1. Recombinant Growth Hormone Antagonist and its Trisulfide Isoform Impurity

Figure 1B:
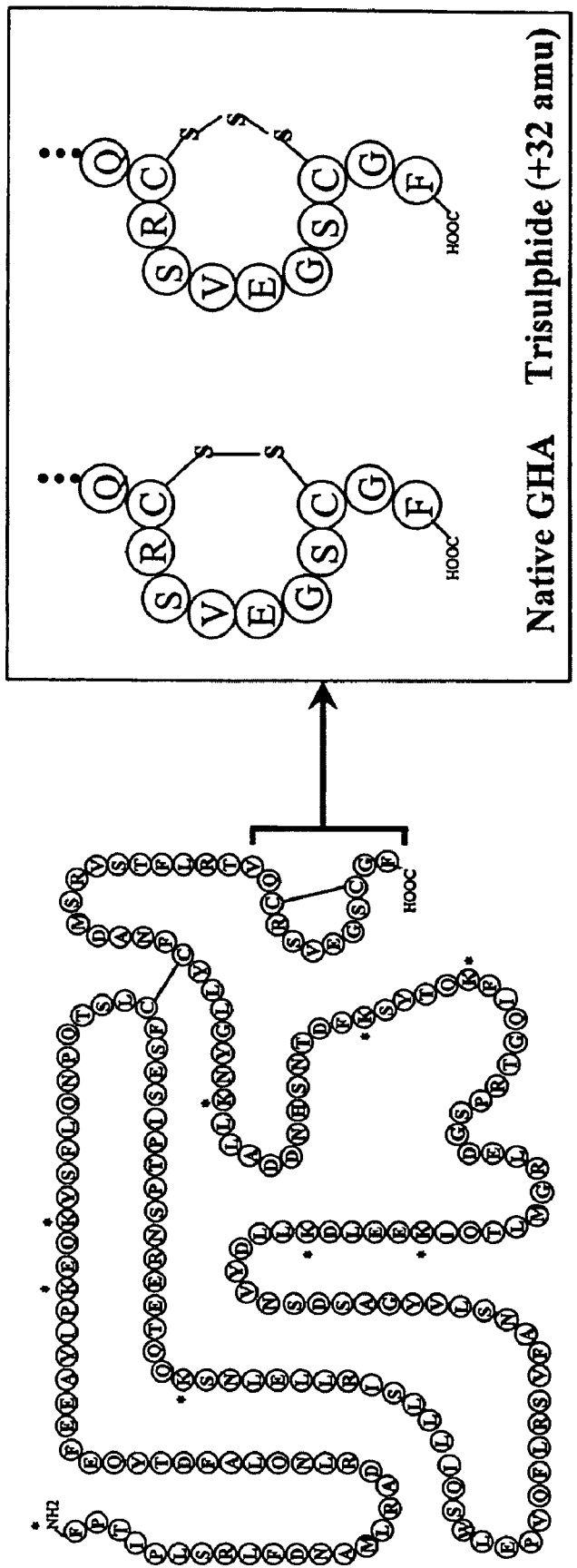
FIG. 1B depicts the structure of the trisulfide isoform impurity of B-2036 [designated "Trisulphide (=amu)"] as compared to its desirable form (designated "Native GHA").

FIG. 1B illustrates the amino acid sequence structure of the trisulfide isoform impurity of B-2036. In particular, the trisulfide isoform impurity contains an extra sulfur atom in the bridge between the cysteines at positions 182 and 189 of the B-2036 protein component.

a. Decrease of Trisulfide Isoform Impurity With Mercapto Compound(s)

Without being bound by theory, it is believed that contact between selected mercapto compound(s) and the trisulfide isoform impurity of the recombinant growth hormone antagonist B-2036 results in converting the cysteine-S—S—

S-cysteine trisulfide bridge back to its cysteine-S—S-cysteine native form. Additionally, also without being bound by theory, it is possible that the presence of the mercapto compound(s) prevents further formation of the trisulfide bridge itself.

Typically, the mercapto compound(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535 and U.S. Pat. No. 5,672,662.

Any mercapto compound may be used in connection with the present invention which, when contacted (preferably, with adequate mixing) with the B-2036 protein component together with its trisulfide isoform impurity, is one that is sufficient to decrease the level of the trisulfide isoform impurity, preferably without degrading (or substantially degrading) the yield of B-2036. Preferred mercapto compounds suitable for use with the present invention include, but are not limited to, sulfites, glutathione, beta-mercaptoethanol, dithiothreitol, mercaptoethylamine, dithioerythritol, tris(2-carboxyethyl) phosphine hydrochloride, cysteine, and cysteine in combination with cystine.

Other suitable mercapto compounds for use with the present invention are noted in the following references: (1) J. Houk and G. M. Whitesides, "Structure-Reactivity Relations for Thiol-Disulfide Interchange," J. M. Chem. Soc., 109: 6825-6836 (1987); (2) Sigmund, M., The Chemistry & Biochemistry of the Sulfhydro Group in Amino Acids, Peptides and Proteins, $1^{st}$ Ed. Pergamon, New York (1973). In particular, see Table II of Houk et al. identified in item (1) above for a listing of exemplary mercapto compounds suitable for use with the present invention.

Of suitable mercapto compounds, cysteine, or cysteine in combination with cystine (dimerized cysteine), is most preferred. The amount of cysteine or combination of cysteine and cystine (dimerized cysteine, if any) that is suitable for use with the present invention should be that amount which is sufficient to decrease the trisulfide isoform impurity by at least about 10% of its highest equilibrium concentration (or its highest average equilibrium concentration, where multiple batches are averaged) formed. Preferably, the decrease in the amount of the trisulfide isoform impurity is least about 20%, 30%, 40%, or 50%, respectively, of its highest equilibrium concentration (or its highest average equilibrium concentration) formed. The initial combined concentration of cysteine and any cystine suitable for use with the present invention is preferably at least about 0.1 mM, from about 0.1 mM to about 10 mM, or from about 1 mM to about 5 mM, respectively.

It is preferred to provide the mercapto compound in a buffer. Preferably, the buffer is one that is suitable for use with the present invention, i.e., does not prevent the formation of the B-2036 protein component or degrade it once it is formed. Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 4 to about 9, from about 7.5 to about 8.5, or from about 7.5 to about 8.0, respectively. Notably, where higher concentrations of mercapto compound are used, higher pH levels, for example, as high as about 9.5 may be tolerated. Thus, for example, if a large excess of cysteine to B-2036 is used, then the pH of the buffer may be as high as about 9.5.

As noted above, it is preferred to provide the mercapto compound in a buffer. Furthermore, the amount of the mercapto compound in the buffer should be such that the molar ratio of the moles of mercapto compound to the moles of B-2036 protein is from about 0.5 to about 1,000. This is especially so when the mercapto compound being used is a combination of cysteine and, optionally, cysteine in combination with cystine. Alternatively, the molar ratio of the moles of mercapto compound to the moles of B-2036 protein may be from about 1 to about 1,000, from about 1 to about 500, or from about 1 to about 10, respectively.

Typically, after sufficient contact (to decrease the level of the trisulfide isoform impurity) between the mercapto compound and the B-2036 protein component (within or from the host cell(s) has been completed), the B-2036 protein component in the buffer has a concentration from about 0.1 mg/ml to about 30 mg/ml, from about 0.5 mg/ml to about 20 mg/ml, or from about 1 mg/ml to about 10 mg/ml, respectively.

Furthermore, the temperature range of the growth medium together with the buffer, the mercapto compound(s) and its other contents including, but not limited to, B-2036, should be maintained at a temperature preferably from about 0° C. to about 25° C. after the mercapto compound has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 8° C., respectively. It is important to note that B-2036 protein denaturation occurs at about 40+° C. As such, it is desirable to maintain the temperature of the homogenate (i.e., containing host cells, growth medium, buffer, mercapto compounds and B-2036, etc.) to a temperature below the protein denaturation temperature of B-2036.

Additionally, the contact time between the B-2036 component and the mercapto compound should be for a time sufficient to decrease the level of the trisulfide isoform impurity. Exemplary suitable contact times for decreasing the level of the trisulfide isoform impurity should be for at least about 30 minutes, from about 1 hour to about 24 hours, or from about 1 hour to about 4 hours, respectively.

Typically, after sufficient contact between the mercapto compound(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the mercapto compound(s) and the B-2036 component include things such as mixing rate. The mixing rate should be that which is sufficient to form a homogenous mixture (of the host cell(s), lysate thereof, buffer, mercapto compound(s), the B-2036 component and any other components in one growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

b. Decrease of Trisulfide Isoform Impurity with Chelating Agent(s)

Without being bound by theory, it is believed that contact between selected chelating agent(s) and (1) the trisulfide isoform impurity, (2) the recombinant growth hormone antagonist B-2036, (3) host cell cellular component(s) (for recombinant production of the antagonist), and (4) all combinations of (1)-(3) results in converting the cysteine-S—S—S-cysteine trisulfide bridge back to its cysteine-S—S-cysteine native form or decreasing levels of the impurity. Additionally, also without being bound by theory, it is possible that the presence of the chelating agent(s) prevents further formation of the trisulfide bridge itself.

Typically, the chelating agent(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any chelating agent may be used in connection with the present invention which, when contacted (preferably with adequate mixing) with the B-2036 protein component together with its trisulfide isoform impurity, is one that is sufficient to decrease the level of the trisulfide isoform impurity, preferably without degrading (or substantially degrading) the yield of B-2036. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, $12^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, $16^{th}$ Ed., Arthur Osol (Editor), Mack Publishing Co., Easton, Pa. (1980) and each and every subsequent edition to date thereof; (3) The United States Pharmacopeia, $21^{st}$ Revision ($16^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the trisulfide isoform impurity by at least about 10% of its highest equilibrium concentration (or its highest average equilibrium concentration, where multiple batches are averaged) formed. Preferably, the decrease in the amount of the trisulfide isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed. Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of B-2036 protein is from about 1 to about 1,000. Alternatively, the molar ratio of the moles of chelating agent to the moles of B-2036 protein may be from about 20 to about 1,000, from about 50 to about 250, or from about 60 to about 110, respectively.

Typically, after sufficient contact (to decrease the level of the trisulfide isoform impurity) between the chelating agent and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, B-2036, should be maintained at a temperature preferably from about 0° C. to about 35° C. after the chelating agent has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the B-2036 rises to about 30° C. upon homogenization. It is important to note that B-2036 protein denaturation occurs at about 40+° C. As such, it is desirable to maintain the temperature of the homogenate (i.e., containing host cells, growth medium, buffer, chelating agents, and B-2036, etc.) to a temperature below the protein denaturation temperature of B-2036.

Additionally, the contact time between the B-2036 component and the chelating agent should be for a time sufficient to decrease the level of the trisulfide isoform impurity. Exemplary suitable contact times for decreasing the level of the trisulfide isoform impurity should be for at least about 30 minutes, from about 1 hour to about 48 hours, or from about 5 hours to about 15 hours, respectively.

Typically, after sufficient contact between the chelating agent(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the B-2036 component include things such as mixing rate. The mixing rate should be that which is sufficient to form a homogenous mixture (of the host cell(s), lysate thereof, buffer, chelating agent(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

c. Decrease of Trisulfide Isoform Impurity with Metal Salt(s)

Without being bound by theory, it is believed that contact between selected metal salt(s) and (1) the trisulfide isoform impurity, (2) the recombinant growth hormone antagonist B-2036, (3) host cell cellular component(s) (for recombinant production of the antagonist), and (4) all combinations of (1)-(3) results in converting the cysteine-S—S—S-cysteine trisulfide bridge back to its cysteine-S—S-cysteine native form or decreasing levels of the impurity. Additionally, also without being bound by theory, it is possible that the presence of the metal salt(s) prevents further formation of the trisulfide bridge itself.

Typically, the metal salt(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any metal salt may be used in connection with the present invention which, when contacted (preferably with adequate mixing) with the B-2036 protein component together with its trisulfide isoform impurity, is one that is sufficient to decrease the level of the trisulfide isoform impurity, preferably without degrading (or substantially degrading) the yield of B-2036. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts are noted in the following references: (1) The Merck Index, $12^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, $16^{th}$ Ed. Arthur Osol (Editor), Mack Publishing Co., Easton, Pa. (1980) and each and every subsequent edition to date thereof; (3) The United States Pharmacopeia, $21^{st}$ Revision ($16^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the trisulfide isoform impurity by at least about 10% of its highest concentration (or its highest average concentration, where multiple batches are averaged) formed. Preferably, the decrease in the amount of the trisulfide isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of B-2036 protein is from about 1 to about 10,000. Alternatively, the molar ratio of the moles of the metal salt to the moles of B-2036 protein may be from about 300 to about 10,000, from about 500 to about 5,000, or from about 500 to about 2500, respectively.

Typically, after sufficient contact (to decrease the level of the trisulfide isoform impurity) between the metal salt(s) and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, B-2036, preferably should be maintained at a temperature from about 0° C. to about 35° C. after the metal salt has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that B-2036 protein denaturation occurs at about 40+° C. As such, it is desirable to maintain the temperature of the homogenate (i.e., containing host cells, growth medium, buffer, metal salt, B-2036, and optionally mercapto compound, etc.) to a temperature below the protein denaturation temperature of B-2036.

Additionally, the contact time between the B-2036 component and the chelating agent should be for a time sufficient to decrease the level of the trisulfide isoform impurity. Exemplary suitable contact times for decreasing the level of the trisulfide isoform impurity should be for at least about 30 minutes, from about 1 hour to about 48 hours, or from about 5 hours to about 15 hours, respectively.

Typically, after sufficient contact between the metal salt(s) and the B-2036 component, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the B-2036 component include things such as mixing rate. The mixing rate should be that which is sufficient to form a homogenous mixture (of the host cell(s), lysate thereof, buffer, metal salt(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

2. Recombinant Growth Hormone Antagonist and its Des-Phe Isoform Impurity a. Decrease of Des-Phe Isoform Impurity With Chelating Agent Without being bound by theory, it is believed that addition of chelating agent(s) to the recombinant growth hormone antagonist B-2036 results in a decrease in the level of the des-phe isoform impurity either by an actual reduction in the level thereof and/or prevention of further des-phe formation.

Typically, the chelating agent(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any chelating agent may be used in connection with the present invention which, when contacted (preferably with adequate mixing) with the B-2036 protein component together with its des-phe isoform impurity, is one that is sufficient to decrease the level of the des-phe isoform impurity, preferably without degrading (or substantially degrading) the yield of B-2036. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, 16$^{th}$ Ed., Arthur Osol (Editor), Mack Publishing Co., Easton, Pa. (1980) and each and every subsequent edition to date thereof; (3) The United States Pharmacopeia, 21$^{st}$ Revision (16$^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the des-phe isoform impurity by at least about 10% of its highest equilibrium concentration (or its highest average equilibrium concentration, where multiple batches are averaged) formed. Preferably, the decrease in the amount of the des-phe isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of B-2036 protein is from about 1 to about 1,000. Alternatively, the molar ratio of the moles of chelating agent to the moles of B-2036 protein may be from about 20 to about 1,000, from about 50 to about 250, or from about 60 to about 110, respectively.

Typically, after sufficient contact (to decrease the level of the des-phe isoform impurity) between the chelating agent and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, B-2036, should be maintained at a temperature preferably from about 0° C. to about 35° C. after the chelating agent has been added to the host cell(s) or lysate thereof containing the B-2036 protein component. Also, preferably, the temperature of the host cell(s) and/or lysate therefrom containing the B-2036 component is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the B-2036 rises to about 30° C. upon homogenization. It is important to note that B-2036 protein denaturation occurs at about 40+° C. As such, it is desirable to maintain the temperature of the homogenate (i.e., containing host cells, growth medium, buffer, chelating agents, and B-2036, etc.) to a temperature below the protein denaturation temperature of B-2036.

Additionally, the contact time between the B-2036 component and the chelating agent should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the chelating agent(s) and the B-2036 component, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the B-2036 component include things such as mixing rate. The mixing rate should be that which is sufficient to form a homogenous mixture (of the host cell(s), lysate thereof, buffer, chelating agent(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

b. Decrease of Des Phe Isoform Impurity With Metal Salt

Without being bound by theory, it is believed that addition of metal salt(s) to the recombinant growth hormone antagonist B-2036 results in a decrease in the level of the des-phe isoform impurity either by an actual reduction it he level thereof and/or prevention of further des-phe formation.

Typically, the metal salt(s) is/are added to the host cell(s) synthesizing the desired recombinant B-2036 protein component during or after (or during and after) growth of the host cell(s). Furthermore, after the growing and contacting steps have been conducted, it is preferred to purify the B-2036 protein. Thereafter, the purified protein is preferably pegylated to yield PEG B-2036 (pegvisomant). For pegylation procedures see U.S. Pat. No. 5,849,535.

Any metal salt may be used in connection with the present invention which, when contacted (preferably with adequate mixing) with the B-2036 protein component together with its des-phe isoform impurity, is one that is sufficient to decrease the level of the des-phe isoform impurity, preferably without degrading (or substantially degrading) the yield of B-2036. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts for use with the present invention are noted in the following references: (1) The Merck Index, $12^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, $16^{th}$ Ed. Arthur Osol (Editor), Mack Publishing Co., Easton, Pa. (1980) and each and every subsequent edition to date thereof; (3) The United States Pharmacopeia, $21^{st}$ Revision ($16^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the des-phe isoform impurity by at least about 10% of its highest concentration (or its highest average concentration, where multiple batches are averaged) formed. Preferably, the decrease in the amount of the des-phe isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not degrade the formation of the B-2036 protein component. Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of B-2036 protein is from about 1 to about 10,000. Alternatively, the molar ratio of the moles of the metal salt to the moles of B-2036 protein may be from about 300 to about 10,000, from about 500 to about 5,000, or from about 500 to about 2500, respectively.

Typically, after sufficient contact (to decrease the level of the des-phe isoform impurity) between the metal salt(s) and the B-2036 protein component (within or from the host cell(s) has been completed), the B-2036 protein component in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, B-2036, preferably should be maintained at a temperature from about 0° C. to about 35° C. after the metal salt has been added to the host cell(s) or lysate thereof containing the B-2036 protein component. Also preferably, the temperature of the host cell(s) and/or lysate therefrom containing the B-2036 component is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that B-2036 protein denaturation occurs at about 40+° C. As such, it is desirable to maintain the temperature of the homogenate (i.e., containing host cells, growth medium, buffer, metal salt, B-2036, and optionally mercapto compound, etc.) to a temperature below the protein denaturation temperature of B-2036.

Additionally, the contact time between the B-2036 component and the metal salt should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the metal salt(s) and the B-2036 component, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the B-2036 component include things such as mixing rate. The mixing rate should be that which is sufficient to form a homogenous mixture (of the host cell(s), lysate thereof, buffer, metal salt(s), the B-2036 component and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the B-2036 protein component is minimized.

3. Recombinant Growth Hormone and its Des-Phe Isoform Impurity a. Decrease of Des-Phe Isoform Impurity With Chelating Agent Without being bound by theory, it is believed that addition of chelating agent(s) to the recombinant growth hormone results in a decrease in the level of the des-phe isoform impurity either by an actual reduction in the level thereof and/or prevention of further des-phe formation.

Typically, the chelating agent(s) is/are added to the host cell(s) synthesizing the desired recombinant growth hormone protein during or after (or during and after) growth of the host cell(s). Furthermore, after the growing and contacting steps have been conducted, it is preferred to purify the growth hormone protein.

Any chelating agent may be used in connection with the present invention which, when contacted (preferably with adequate mixing) with the growth hormone protein together with its des-phe isoform impurity, is one that is sufficient to decrease the level of the des-phe isoform impurity, preferably without degrading (or substantially degrading) the yield of the growth hormone. Preferred chelating agents suitable for use with the present invention include, but are not limited to, EDTA, EGTA, and DTPA. Additional exemplary chelating agents include, but are not limited to, Deferoxamine, Ditiocarb Sodium, Edetate Calcium Disodium, Edetate Disodium, Edetate Sodium, Edetate Trisodium, Penicillamine, Pentetate Calcium Trisodium, Pentetic Acid, Succimer, and Trientine. Note that Edetate Sodium is the salt form of EDTA.

Other suitable chelating agents for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, 16$^{th}$ Ed., Arthur Osol (Editor), Mack Publishing Co., Easton, Pa. (1980) and each and every subsequent edition to date thereof; (3) The United States Pharmacopeia, 21$^{st}$ Revision (16$^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable chelating agents, EDTA is most preferred. The amount of chelating agent that is suitable for use with the present invention should be that amount which is sufficient to decrease the des-phe isoform impurity by at least about 10% of its highest equilibrium concentration (or its highest average equilibrium concentration, where multiple batches are averaged) formed. Preferably, the decrease in the amount of the des-phe isoform impurity is least about 20%, 30%, 40%, or 50%, respectively, of its highest equilibrium concentration (or its highest average equilibrium concentration) formed. The initial concentration of EDTA suitable for use with the present invention is preferably at least about 0.01 mM, from about 0.01 mM to about 100 mM, from about 0.1 mM to about 20 mM, from about 2 mM to about 10 mM or from about 2 to about 5 mM, respectively.

It is preferred to provide the chelating agent in a buffer. Preferably, the buffer is one that is suitable for use with the present invention, i.e., does not prevent the formation of the B-2036 protein component or degrade it once it is formed. Suitable buffers for use in connection with the present invention include, but are not limited to, Tris, phosphate, HEPES, citric acid, triethylamine, and histidine. The preferred buffer is Tris. The preferred initial buffer concentration is from about 1 mM to about 200 mM, more preferably from about 5 mM to about 100 mM, even more preferably from about 8 mM to about 70 mM, and most preferably from about 10 mM to about 50 mM. Other suitable buffers may be used. Preferably, these buffers are sufficient to maintain the pH of the growth medium anywhere in the range from about 6 to about 9, from about 6.5 to about 7.5, or from about 7.2 to about 7.5, respectively.

As noted above, it is preferred to provide the chelating agent in a buffer. Furthermore, the amount of the chelating agent in the buffer should be such that the molar ratio of the moles of chelating agent to the moles of growth hormone protein (e.g., hGH) is from about 1 to about 1,000. Alternatively, the molar ratio of the moles of chelating agent to the moles of growth hormone protein (e.g., hGH) may be from about 20 to about 1,000, from about 50 to about 250, or from about 60 to about 110, respectively.

Typically, after sufficient contact (to decrease the level of the des-phe isoform impurity) between the chelating agent and the growth hormone protein (e.g., hGH) (within or from the host cell(s) has been completed), the growth hormone protein (e.g., hGH) in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the chelating agent(s) and its other contents including, but not limited to, the growth hormone protein, preferably should be maintained at a temperature preferably from about 0° C. to about 35° C. after the chelating agent has been added to the host cell(s) or lysate thereof containing the growth hormone protein. Also, preferably, the temperature of the host cell(s) and/or lysate therefrom containing the growth hormone protein is maintained from about 1° C. to about 15° C., from about 2° C. to about 10° C., or from about 2° C. to about 15° C., respectively. Note that, preferably, upon addition of the chelating agent (e.g., EDTA), the temperature of which is about 4° C., the temperature of the homogenate containing the growth hormone rises to about 30° C. upon homogenization. It is important to note that growth hormone protein denaturation occurs at about 40+° C. As such, it is desirable to maintain the temperature of the homogenate (i.e., containing host cells, growth medium, buffer, chelating agents, and growth hormone protein, etc.) to a temperature below the protein denaturation temperature of growth hormone protein.

Additionally, the contact time between the growth hormone protein and the chelating agent should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the chelating agent(s) and the growth hormone protein, the buffer containing the same has a volume from about 1 liter to about 5,000 liters, from about 10 liters to about 500 liters, or from 100 liters to about 300 liters, respectively. Other suitable exemplary volumes may be anywhere from 160 liters to about 500 liters.

Other parameters that may be of interest during contact between the chelating agent(s) and the growth hormone protein include things such as mixing rate. The mixing rate should be that which is sufficient to form a homogenous mixture (of the host cell(s), lysate thereof, buffer, chelating agent(s), the growth hormone protein and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the growth hormone protein component is minimized.

b. Decrease of Des-Phe Isoform Impurity With Metal Salt

Without being bound by theory, it is believed that addition of metal salt(s) to the recombinant growth hormone results in a decrease in the level of the des-phe isoform impurity either by an actual reduction in the level thereof and/or prevention of further des-phe formation.

Typically, the metal salt(s) is/are added to the host cell(s) synthesizing the desired recombinant growth hormone protein component during or after (or during and after) growth of the host cell(s). Furthermore, after the growing and contacting steps have been conducted, it is preferred to purify the growth hormone protein.

Any metal salt may be used in connection with the present invention which, when contacted (preferably with adequate mixing) with the growth hormone protein component together with its des-phe isoform impurity, is one that is sufficient to decrease the level of the des-phe isoform impurity, preferably without degrading (or substantially degrading) the yield of growth hormone. Metal salt(s) suitable for use with the present invention include, but are not limited to, alkali earth metal salt(s), alkaline earth metal salt(s), transition metal salt(s) and combinations thereof. Preferred metal salts suitable for use with the present invention include, but are not limited to, potassium phosphate, potassium acetate, sodium phosphate, sodium acetate, zinc chloride, and combinations thereof.

Other suitable metal salts for use with the present invention are noted in the following references: (1) The Merck Index, 12$^{th}$ Edition, S. Budavari (Editor), Merck & Co., Inc., Therapeutic Category and Biological Activity Index, p. THER-19 (under "CHELATING AGENT"), Whitehouse Station, N.J. (1996) and each and every subsequent edition to date thereof; (2) Remington's Pharmaceutical Sciences, 16$^{th}$ Ed. Arthur Osol (Editor), Mack Publishing Co., Easton, Pa. (1980) and each and every subsequent edition to date thereof; (3) The United States Pharmacopeia, 21$^{st}$ Revision (16$^{th}$ Edition), United States Pharmacopeial Convention, Inc., Rockville, Md. (1985) and each and every subsequent edition to date thereof; (4) SIGMA, Biochemicals and Reagents for Life Science Research Catalogue, St. Louis, Mo. (2002-2003); and (5) Aldrich, Handbook of Fine Chemicals and Laboratory Equipment, Milwaukee, Wis. (2000-2001) and (2002-2003) editions thereof.

Of suitable metal salts for use with the present invention sodium phosphate, $ZnCl_2$ and combinations thereof are also preferred. The amount of metal salt(s) suitable for use with the present invention should be that amount which is sufficient to decrease the des-phe isoform impurity by at least about 10% of its highest concentration (or its highest average concentration, where multiple batches are averaged) formed. Preferably, the decrease in the amount of the des-phe isoform impurity is least about 20%, 30%, 40%, or 50%, respectively, of its highest concentration (or its highest average concentration) formed. The initial concentration of metal salt (e.g., sodium phosphate) suitable for use with the present invention is preferably at least about 0.1 mM, from about 1 mM to about 500 mM, from about 1 mM to about 200 mM, from about 5 mM to about 175 mM, from about 10 mM to about 150 mM or from about 25 to about 100 mM, respectively.

It is preferred to provide the metal salt in a buffer. However, sodium phosphate can act both as a buffer and a suitable metal salt. However, additional suitable metal salt(s) may be added to the sodium phosphate buffer. Preferably, the buffer is one that is suitable for use with the present invention, i.e., does not prevent the formation of the B-2036 protein component or degrade it once it is formed Suitable buffers for use in connection with the present invention include, but are not limited to, Tris, phosphate, HEPES, citric acid, triethylamine, and histidine. The preferred initial buffer concentration is from about 1 mM to about 200 mM, more preferably from about 5 mM to about 100 mM, even more preferably from about 8 mM to about 70 mM and most preferably from about 10 mM to about 50 mM. Other suitable buffers may be used. Preferably, these buffers are sufficient to maintain the pH of the growth medium anywhere in the range from about 4 to about 9, from about 4.5 to about 7.5, or from about 5.5 to about 7.5, respectively.

After the metal salt is provided in a buffer (or in the case of NaP, where the NaP solution acts both as the metal salt and the buffer), the amount of the metal salt in the buffer (or NaP solution also acting as the buffer) should be such that the molar ratio of the moles of metal salt to the moles of growth hormone protein (e.g., hGH) is from about 1 to about 10,000. Alternatively, the molar ratio of the moles of the metal salt to the moles of growth hormone protein (e.g., hGH) may be from about 300 to about 10,000, from about 500 to about 5,000, or from about 500 to about 2500, respectively.

Typically, after sufficient contact (to decrease the level of the des-phe isoform impurity) between the metal salt(s) and the growth hormone protein (e.g., hGH) (within or from the host cell(s) has been completed), the growth hormone protein in the buffer has a concentration from about 0.1 mg/ml to about 20 mg/ml, from about 0.5 mg/ml to about 5 mg/ml, or from about 1 mg/ml to about 5 mg/ml, respectively.

Furthermore, the temperature range of the growth medium together with the buffer, the metal salt(s) and its other contents including, but not limited to, the growth hormone protein, preferably should be maintained at a temperature from about 0° C. to about 35° C. after the metal salt has been added to the host cell(s) or lysate thereof containing the growth hormone protein. Also, preferably, the temperature of the host cell(s) and/or lysate therefrom containing the growth hormone protein is maintained from about 1° C. to about 15° C., from about 2° C. to about 10° C., or from about 2° C. to about 15° C., respectively. Note that upon homogenization with the metal salt (e.g., NaP), the temperature of the homogenate may rise. It is important to note that growth hormone protein denaturation occurs at about 40+° C. As such, it is desirable to maintain the temperature of the homogenate (i.e., containing host cells, growth medium, buffer, metal salt, growth hormone protein, and optionally mercapto compound, etc.) to a temperature below the protein denaturation temperature of growth hormone protein.

Additionally, the contact time between the growth hormone protein and the metal salt should be for a time sufficient to decrease the level of the des-phe isoform impurity. Exemplary suitable contact times for decreasing the level of the des-phe isoform impurity should be for at least about 30 minutes, from about 1 hour to about 48 hours, or from about 5 hours to about 15 hours, respectively.

Typically, after sufficient contact between the metal salt(s) and the growth hormone protein, the buffer containing the same has a volume from about 1 liter to about 5,000 liters, from about 100 liters to about 2,000 liters, or from 200 liters to about 1,500 liters, respectively.

Other parameters that may be of interest during contact between the metal salt(s) and the growth hormone protein include things such as mixing rate. The mixing rate should be that which is sufficient to form a homogenous mixture (of the host cell(s), lysate thereof, buffer, metal salt(s), the growth hormone protein and any other components in the growth medium) while minimizing the amount of foaming that may be formed. Those of ordinary skill can readily determine what a sufficient mixing rate should be. Obviously, the mixing rate should be such that the temperature is maintained in the above-noted ranges and any degradation of the growth hormone protein component is minimized.

4. Pegylated Polypeptide and its Aggregate a. Decrease of Aggregate With Anion Exchange Chromatography In manufacturing and purifying B-2036 PEG, the bulk intermediate or B-2036 molecule is prepared as noted above. Thereafter, the B-2036 molecule is processed according to the following six steps to yield final API which is the B-2036 PEG protein of interest. These six steps are as follows:

1. pegylation to yield pegylated B-2036,
2. HIC chromatography (optional step) to yield an HIC pool,
3. ultrafiltration/diafiltration (optional step) to yield a diafiltration pool,
4. AEX chromatography together with pooling to yield an AEX pool,
5. diafiltration of the AEX pool to yield a diafiltration pool, and
6. API filtration (for sterilization purposes, preferably, through a 0.22 micron filter into collection bottles for freezing) to yield a final API.

The above-noted steps 1-6 are exemplary and disclosed in flowchart 1 and Example 1.

Referring to step 1, the pegylation step accomplishes the first step of the claimed invention of providing pegylated protein isoforms of interest. Thereafter, the HIC step 2 and the subsequent diafiltration step 3, both of which are considered optional, are preferably conducted to remove any unpegylated protein, free PEG molecules, or any other impurities that may be removed during step 2. After step 3, the diafiltration pool of step 3 is then subjected to anion exchange chromatography of step 4 to separate the PEG-1, PEG-2, PEG-3, PEG-4, PEG-5, PEG-6, PEG-7, PEG-8 and PEG-9 isoforms which are then subsequently pooled to preferably enrich the level of PEG-4, PEG-5 and PEG-6 isoforms into a final product for further processing in step of the diafiltration to be followed by the sterilization filtration of step 6 to yield a final API product.

Referring now back to the pegylation step 1, the B-2036 molecule is subjected to conditions sufficient for pegylating the B-2036 molecule itself into B-2036 PEG including the PEG-1, PEG-2, PEG-3, PEG-4, PEG-5, PEG-6, PEG-7, PEG-8 and PEG-9 isoforms. The preferred pegylation parameters are provided in flowchart 1 and Example 1. The B-2036 molecule and any other molecules to which PEG molecules may be attached, preferably, by covalent attachment are PEG molecules selected from the group consisting of PEG-N-hydroxysuccinimide-5K, PEG-succinimidyl carbonate-5K, PEG-succinimidyl propionate-5K, PEG2-malemide-40K (2×20K), PEG2-N-hydroxysuccimide-40K (2×20K), and PEG2-aldehyde-40K (2×20K). The amount of the PEG molecule added to the B-2036 molecule for pegylation (or any other protein of interest which needs to be pegylated) should be such that the stoichiometric weight ratio of the amount of free (unbound) PEG molecules to the amount of unpegylated protein molecules is from about 0.5 to about 100, preferably from about 1.5 to about 2.5, more preferably from about 1.9 to about 2, and most preferably from about 1.95 to about 2.05. During pegylation, the B-2036 molecule (or any other protein of interest to be pegylated) is pegylated at a pegylating pH from about 3 to about 10, preferably from about 7.2 to about 7.8, more preferably from about 7.4 to about 7.8, and most preferably from about 7.40 to about 7.80. The temperature at which the pegylating step is conducted is referred to as a pegylating temperature. The pegylating temperature is from about 0° C. to about 40° C., preferably from about 10° C. to about 30° C., and more preferably from about 18° C. to about 25° C.

Now referring to the optional HIC step 2, the preferred parameters for conducting this step are provided in Example 1 and in flowchart 1. During the optional HIC chromatography step 2, the pegylated protein and any unpegylated protein is loaded onto the HIC resin at an HIC load of ≦about 10 g protein per liter of packed bed volume of HIC resin, preferably ≦about 5 gram protein per liter of packed bed volume of HIC resin, or ≦about 4.1 g protein per liter of packed volume of HIC resin. Also, the HIC loading conductivity is from about 30 to about 60 mS/cm, preferably from about 40 to about 52 mS/cm, or more preferably from about 45 to about 51 mS/cm. Furthermore, the HIC step is conducted at an HIC temperature from about 10 to about 40° C., preferably from about 15 to about 30° C. and most preferably from about 18 to about 25° C. The optional HIC step 2 removes at least some free PEG, unpegylated protein and aggregate, respectively, present on HIC loading.

Following HIC step 2, an HIC pool is obtained. The HIC pool is then subjected to an ultrafiltration/diafiltration step 3 which is optional in the sense that if the HIC step 2 is conducted then the ultrafiltration/diafiltration steps is also conducted. However, if the HIC step 2 is not conducted, then there is no need to conduct the ultrafiltration/diafiltration step 3. Alternatively, ultrafiltration/diafiltration step 3 can still be conducted in the absence of optional HIC step 2. The preferred conditions under which the ultrafiltration/diafiltration step 3 is conducted are noted in Example 1 and in flowchart 1. Herein, we refer to this step as UF/DF #3. The UF/DF #3 step is conducted with a UF/DF #3 membrane having a molecular weight cutoff (MWCO) from about 3 kDa to about 20 kDa, preferably from about 8 kDa to about 15 kDa, more preferably from about 10 kDa to about 12 kDa, and most preferably about 10 kDa.

After step 3, the product obtained at this point is referred to as the diafiltration pool. This diafiltration pool is then subjected to step 4 which is the anion exchange chromatography and pooling step. Preferred conditions for performing this AEX chromatography and pooling step are provided in Example 1 and in flowchart 1. The diafiltration pool of the previous step (i.e., step 3) or the pegylated protein (e.g., B-2036 PEG of step 1, if steps 2 and 3 have not been conducted) is subjected to step 4. In effect, without HIC processing of step 2, the diafiltration pool of step 3 containing B-2036 PEG or the B-2036 PEG of step 1 is loaded onto an anion exchange resin together with any free PEG, any pegylated protein, unpegylated protein, partially pegylated protein, and any impurity (such as the trisulfide impurity or the des-phe impurity) and any aggregate thereof.

Preferably, the resin used is an anion exchange (AEX) resin. Preferred AEX resins include, but are not limited to, ANX4, DEAE, Q-Sepharose, Q-Sepharose FF, Q-Sepharose HP, and Q-Sepharose XL. The preferred AEX resin is Q-Sepharose FF.

Preferably, the AEX resin comprises functional groups selected from the group consisting of primary, secondary, tertiary, quaternary amines and combinations thereof. Additionally, the AEX resin comprises functional groups selected from the group consisting of diethylaminoethyl, diethylaminopropyl, dimethylethanolamine, trimethyl-ammoniumethyl, trimethylbenzyl ammonium, dimethylethanol benzyl and polyamine functional groups. Furthermore, the AEX resin preferably comprises a support material selected from the group consisting hydrophilic polyether, crosslinked divinyl benzene polystyrene, crosslinked agarose, polypropylene, hydrophilic acrylamidovinyl, methacrylic, polymerized hydrogel with a ceramic bead base, composite silica-dextran material, polymer grafted silica, divinyl benzene styrene, divinyl benzene polyacrylic, crosslinked cellulose, co-polymer methacrylate, polystyrene, acrylic, G5000 hydrophilic gel, and cellulose. Also, it is preferred to use an AEX resin which comprises a macroporous resin or a gel resin. Typically, the support material has a diameter from about 10 to about 500 μm, and preferably about 30 μm.

The AEX loading is conducted at an AEX loading conductivity which is ≦about 10 mS/cm, preferably ≦about 5 mS/cm, and most preferably ≦about 2.4 mS/cm. The AEX resin is loaded at an AEX loading pH from about 5 to about 10, preferably from about 6.6 to about 9, more preferably from about 6.9 to about 7.1.

The load of the pegylated protein including any impurity such as the trisulfide impurity or des-phe impurity or aggregate thereof is such that the AEX load is ≦10 g protein/L of packed bed volume of AEX resin, preferably ≦5.5 g protein/L of packed bed volume of AEX resin, more preferably ≦about 4.1 g protein/L of packed bed volume of AEX resin.

According to one embodiment, the pegylated protein that is loaded onto the AEX resin or that is provided in the first step of providing a pegylated protein includes one or more pegylated protein isoforms, PEG-1, PEG-2, PEG-3, PEG-4, PEG-5, PEG-6, PEG-7, PEG-8, PEG-9 and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-2, PEG-3, PEG-4, PEG-5, PEG-6, PEG-7, PEG-8 and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-2, PEG-3, PEG-4, PEG-5, PEG-6, PEG-7, PEG-8 and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-3, PEG-4, PEG-5, PEG-6, PEG-7, PEG-8 and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-4, PEG-5, PEG-6, PEG-7, PEG-8 and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-4, PEG-5, PEG-6, PEG-7, and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-4, PEG-5, PEG-6, and any aggregate, trisulfide impurity and des-phe impurity thereof and any unpegylated impurity of the pegylated protein and any free PEG molecules.

According to another embodiment, the pegylated protein that is loaded onto the AEX resin or that is provided in the first step of providing a pegylated protein includes one or more pegylated protein isoforms, PEG-4, PEG-5, PEG-6, and any aggregate, trisulfide impurity and des-phe impurity thereof and any unpegylated impurity of the pegylated protein.

According to another embodiment, the pegylated protein that is loaded onto the AEX resin or that is provided in the first step of providing a pegylated protein includes one or more pegylated protein isoforms, PEG-1, PEG-2, PEG-3, PEG-4, PEG-5, PEG-6, PEG-7, PEG-8 and PEG-9 and any aggregate, trisulfide impurity and des-phe impurity thereof.

According to another embodiment, the pegylated protein that is loaded onto the AEX resin or that is provided in the first step of providing a pegylated protein includes one or more pegylated protein isoforms, PEG-1, PEG-2, PEG-3, PEG-4, PEG-5, PEG-6, PEG-7, PEG-8 and PEG-9 and any aggregate, trisulfide impurity thereof.

According to another embodiment, the pegylated protein that is loaded onto the AEX resin or that is provided in the first step of providing a pegylated protein includes one or more pegylated protein isoforms, PEG-1, PEG-2, PEG-3, PEG-4, PEG-S, PEG-6, PEG-7, PEG-8 and PEG-9 and any aggregate thereof.

The pegylated protein together with any aggregate, trisulfide, and/or des-phe impurity thereof, any unpegylated or partially pegylated protein and any free PEG is, after loading onto the AEX resin, subjected to being eluted with an eluting solution during an eluting step followed by collection of the eluent in multiple fractions. The fractions are volume fractions of column volume. The eluting step may be conducted either by a pH gradient or an ionic strength gradient. If the eluting is conducted with an ionic strength gradient, the eluting is done with a salt solution in an eluting buffer containing an ionic salt at a salt concentration sufficient to elute the loaded pegylated protein from the AEX resin. Preferably, the ionic salt is a chloride salt. More preferably the ionic salt is selected from the group consisting of NaCl, lithium chloride, Na phosphate, Na sulfate, ammonium chloride, ammonium sulfate, ammonium phosphate, KI, and KCl. Other suitable ionic salts are recognized for use with AEX resins and are incorporated as if stated here. Preferably, the ionic salt is sodium chloride provided in a buffer. During eluting with a salt solution provided in an eluting buffer, the salt concentration gradient (e.g., for an NaCl salt solution) is from about 2 to about 50 mM per CV, preferably from about 5 to about 25 mM per CV, and more preferably from about 10 to about 20 mM per CV and most preferably from about 10 to about 12.5 mM per CV. The eluting buffer in which the salt solution is provided has a pH from about 5 to about 10, preferably from about 6.6 to about 9, and most preferably from about 6.9 to about 7.1. Furthermore, the eluting step is conducted at an eluting temperature $\leq$ about 50° C., preferably $\leq$ about 35° C., more preferably from about 2 to about 30° C., even more preferably from about 15 to about 30° C. and most preferably from about 18 to about 25° C.

The eluting buffer containing the salt solution is introduced into the AEX resin column and flowed through the column at a linear velocity of $\leq$ 300 cm/hr., preferably from about 10 to about 150 cm/hr., more preferably from 30 to about 100 cm/hr., even more preferably from about 50 to about 100 cm/hr., yet even more preferably from about 50 to about 70 cm/hr., yet even further more preferably from about 60 to about 65 cm/hr., and most preferably at about 60 cm/hr.

When collecting eluent from the AEX resin, it is preferred to collect the eluent in multiple volume fractions ranging from about 0.1 to about 5 column volumes (CV), preferably from about 0.1 to about 1 CV fractions, more preferably from about 0.1 to about 0.5 CV, and most preferably from about 0.1 to about 0.2 CV volume fractions. Thus, for example, one may collect 100 separate fractions which number may be less or more depending on the total amount of salt solution and the eluting buffer sent through the AEX resin to collect the various CV fractions. It is to be understood that the CV fractions are collected serially as eluent is collected at the outlet (typically at the bottom of the AEX column) of the AEX column.

Each of the collected CV fractions will preferably contain a given pegylated protein isoform such as PEG-1, PEG-2, PEG-3, PEG-4, PEG-5, PEG-6, PEG-7, PEG-8 and PEG-9. The collected CV fractions are then subjected to pooling to determine which fraction contains which pegylated protein isoform and then to permit one to selectively combine the desired pegylated protein isoforms so collected.

b. Pooling

Thus, the CV fractions collected from the AEX resin are then subjected to a pooling step to select discrete amounts of the pegylated protein isoforms such as PEG-1, PEG-2, PEG-3, PEG-4, PEG-5, PEG-6, PEG-7, PEG-8, and PEG-9. Various analytical techniques may be used to selectively pool the desired pegylated protein isoforms. These techniques include, but are not limited to, CE, SDS-PAGE, IEX chromatography, HIC chromatography, AEX chromatography, CEX chromatography, RPHPLC, SEHPLC, affinity chromatography (AC), and combinations thereof. Either CE or RPHPLC is preferred over SDS-PAGE. Further, without being bound by theory, it is believed that the reagent (e.g., sodium dodecyl sulfate) used with SDS-PAGE obscure the measurement of any aggregate formed. It is believed that the sodium dodecyl sulfate (SDS) used in the SDS-PAGE assay destroys the aggregate such that a reduced amount of aggregate is measured or no amount of aggregate is measured. However, SDS-PAGE can be successfully used to fingerprint (e.g., determining the PEG-1, PEG-2, PEG-3, PEG-4, PEG-5, PEG-6, PEG-7, PEG-8 and PEG-9 qualitative and quantitative composition of a collected fraction) the individual pegylated proteins. When analysis by CE is conducted for pooling, the analysis is conducted at a CE temperature from about 5 to about 50° C., preferably from about 5 to about 45° C., more preferably from about 20 to about 40° C., and most preferably from about 30 to about 32° C.

Also, when CE is used, the CE is conducted at a CE pooling conductivity (refers to the conductivity of the sample fraction) from about 0 to about 60 mS/cm and more preferably from about 5 to about 10 mS/cm. The sample fraction having a conductivity within the above-noted CE pooling conductivity ranges is then introduced into the CE capillary for pegylated protein fingerprinting. The so-obtained pegylated protein isoform fingerprint of the relevant CV fraction is compared against a reference standard to identify the particular pegylated protein isoform present in that sample.

The area percent obtain by each of fingerprint peak is proportional to the weight % of the isoform corresponding to that peak in that fraction. Then the fraction so identified by CE to contain the desired pegylated protein isoform in the desired weight % of the isoform is then optionally mixed with other fractions similarly selected to yield the desired isoform mixture. This processing yields API composition.

See, for example, Swapan K. Chowdhury et al., "Fingerprinting Proteins Coupled with Polymers by Mass Spectrometry: Investigation of Polyethylene Glycol-Conjugated Superoxide Dismutase," *American Society for Mass Spectrometry*, Vol. 6, pp. 478-487, 1995.

For conducting CE analysis on the CV fraction collected, the pegylated protein concentration in buffer is at least about 0.2 mg/ml, at least about 0.5 mg/ml, from about 0.1. to about 100 mg/ml, from about 0.5 to about 10 mg/l, or from about 2 to about 3 mg/ml, respectively. Using CE, or any of the above-noted analysis techniques for pooling, various pegylated protein isoforms may be combined to yield a desired pool of the pegylated protein. Thus, for example, a pooled pegylated protein may comprise one or more of PEG-1 to PEG-9, one or more of PEG-2 to PEG-9, one or more of PEG-3 to PEG-9, one or more of PEG-3 to PEG-8, one or more of PEG-3 to PEG-7, one of PEG-3 to PEG-6, one or more of PEG-4 to PEG-6, one or more of PEG-4 and PEG-5, one or more of PEG-5 and PEG-6, and PEG-5, respectively.

Among the above-noted pools, various pools of pegylated proteins are preferred. For example, with respect to a pool of PEG-4, PEG-5 and PEG-6, the pool of PEG-4, PEG-5, and PEG-6 should be one that comprises at least 70% by weight of PEG-4, PEG-5, and PEG-6 based on a total weight of the pegylated protein isoforms in that particular pool. Preferably, the pegylated protein fraction of PEG-4, PEG-5, and PEG-6 is at least about 75% by weight based on a total weight of the pegylated protein isoforms present in the pool. This value is more preferably at least about 80% by weight, at least about 85% by weight, at least about 90% by weight and at least about 94% by weight, at least about 95% by weight, at least about 96% by weight, at least about 97% by weight, at least about 98% by weight, at least about 99% by weight, at least about 99.5% by weight, and at least about 99.9% by weight, respectively.

For pooling, the pooling is conducted on the pegylated protein isoforms collected in the CV fractions where the pegylated protein isoforms are provided in a buffer. That buffer in which the pegylated protein isoforms are provided has a pH from about 5 to about 10, preferably from about 6.6 to about 9, and more preferably from about 6.9 to about 7.1. Further, that buffer is one selected from the group consisting of Tris, phosphate, HEPES, citric acid, triethylamine, and histidine.

At this point the pooled pegylated protein isoforms processed according to the above-noted methodology (also discussed in Examples 1, 3 and 4 discussed below) should be such that the aggregate level of the pooled product is ≦about 10% by weight based on a total weight of the pegylated protein isoforms and any aggregate thereof that were subjected to steps 1-5 noted above with steps 2 and 3 being optional. Preferably, the level of the aggregate is ≦about 9%, 8%, 7%, 6%, 5%, 4%, 3%, 2%, 1.5%, 1%, 0.9%, 0.8%, 0.7%, 0.6%, 0.5%, 0.4%, 0.3%, 0.2%, 0.1%, 0.05% and 0.01% by weight based on the above-noted total weight, respectively.

The so-pooled pegylated protein preferably consists essentially of one or more of PEG-1, PEG-2, PEG-3, PEG-4, PEG-5, PEG-6, PEG-7, PEG-8, and PEG-9. The so-pooled pegylated protein preferably consists essentially of one or more of PEG-2, PEG-3, PEG-4, PEG-5, PEG-6, PEG-7, PEG-8, and PEG-9. The so-pooled pegylated protein preferably consists essentially of one or more of PEG-3, PEG-4, PEG-5, PEG-6, PEG-7, PEG-8, and PEG-9. The so-pooled pegylated protein preferably consists essentially of one or more of PEG-3, PEG-4, PEG-5, PEG-6, PEG-7, and PEG-8, The so-pooled pegylated protein preferably consists essentially of one or more of PEG-3, PEG-4, PEG-5, PEG-6, and PEG-7. The so-pooled pegylated protein preferably consists essentially of one or more of PEG-3, PEG-4, PEG-5, and PEG-6. The so-pooled pegylated protein preferably consists essentially of one or more of PEG-4, PEG-5, and PEG-6. The so-pooled pegylated protein preferably consists essentially of one or more of PEG-4, and PEG-5. The so-pooled pegylated protein preferably consists essentially of one or more of PEG-5, and PEG-6. The so-pooled pegylated protein preferably consists essentially of one or more of PEG-5.

The above-noted pooling methodology may be utilized for pooling pegylated protein isoforms independent of whether such isoforms have been subjected to anion exchange chromatography.

Where the pegylated protein is a pegylated growth hormone antagonist, it is preferred that the level of aggregate is ≦6% by weight based on a total weight of the pegylated growth hormone antagonist isoforms and any aggregate thereof in the pool or the collected CV fraction. More preferably the level of aggregate is ≦about 5%, 4%, 3%, 2%, and 1% by weight based on the above-noted total weight, respectively. Furthermore, where the pegylated protein is a pegylated growth hormone antagonist with various isoforms thereof, the "total level" of a sum of any trisulfide impurity, any des-phe impurity and any aggregate thereof is preferably at a level to ≦about 15% by weight based on a total weight of the pegylated growth hormone antagonist isoforms, any trisulfide impurity, any des-phe impurity and any aggregate thereof in the pool or the collected CV fraction. Preferably, the above-noted total level (of a sum of any trisulfide impurity, any des-phe impurity and any aggregate thereof) is ≦about 12%, 10%, 9%, 8%, 7%, 6%, 5%, 4%, 3%, 2% and 1% by weight based on the total weight, respectively.

Also preferably, where the pegylated protein growth hormone antagonist is B-2036 PEG, its polypeptide backbone is B-2036 of SEQ. ID NO. 1. Likewise, also preferably, where the pegylated protein is growth hormone agonist, of its polypeptide backbone is a polypeptide of SEQ. ID NO. 2.

After step 4 of AEX chromatography and pooling, a follow-up ultrafiltration/diafiltration step 5 is conducted. Preferred parameters for conducting this UF/DF step 5 are provided in Example 1 and flowchart 1. At the end of step 5, a diafiltration pool is collected. This diafiltration pool is then subjected to step 6 which is to take the active pharmaceutical ingredient so obtained in the above-noted diafiltration pool and to sterilize it, preferably, by filtration through a 0.22 μm filter. Preferred parameters for conducting the API filtration step 6 are provided in Example 1 and flowchart 1.

Figure 2:
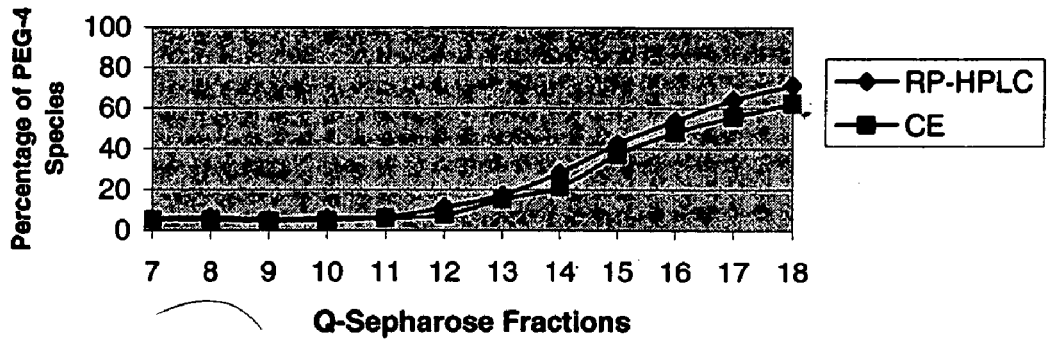
FIG. 2 is a graphic comparison of the percentages of B-2036 PEG 4 species found within Q-Sepharose FF fractions 7 through 18 as determined by capillary electrophoresis and reversed-phase HPLC.
Figure 3:
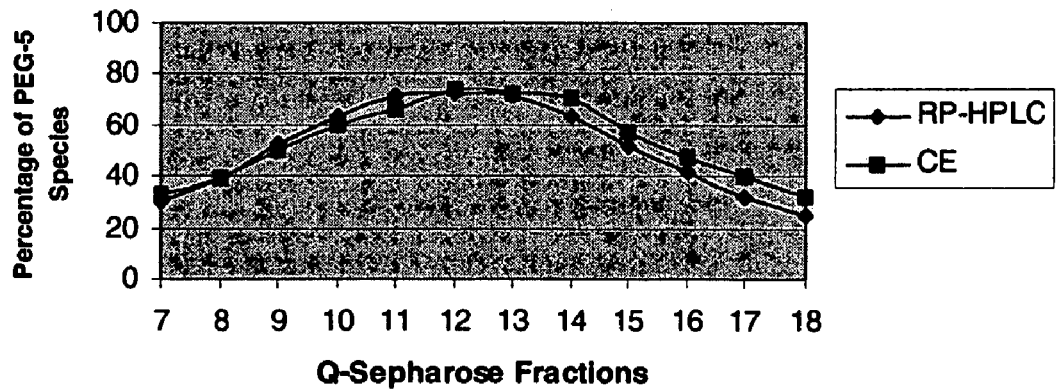
FIG. 3 is a graphic comparison of the percentages of B-2036 PEG 5 species found within Q-Sepharose FF fractions 7 through 18 as determined by capillary electrophoresis and reversed-phase HPLC.
Figure 4:
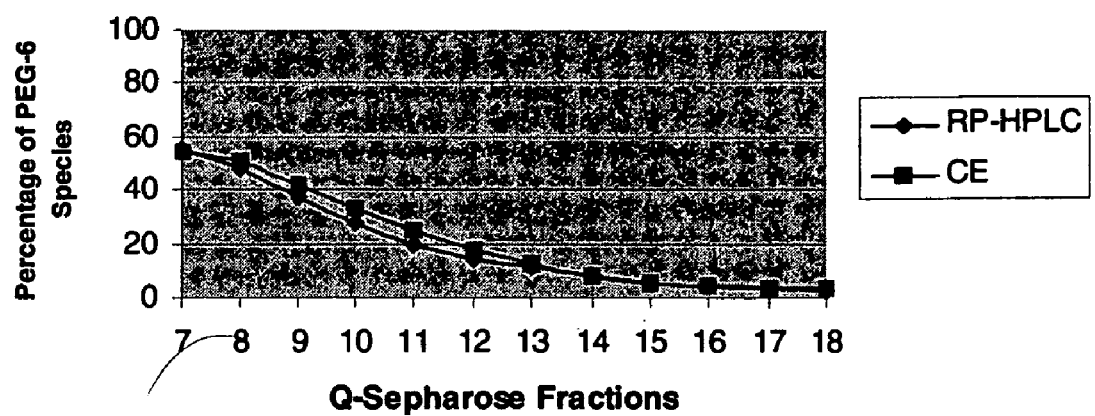
FIG. 4 is a graphic comparison of the percentages of B-2036 PEG 6 species found within Q-Sepharose FF fractions 7 through 18 as determined by capillary electrophoresis and reversed-phase HPLC.

Finally, in Example 1 below, a preferred procedure for the claimed invention is provided reciting the details of each of steps 1-6 noted above, using an anion exchange resin chromatography step. For comparative purposes, a comparative Example 2 is provided wherein the anion exchange chromatography step is replaced with a cation exchange chromatography step together with the appropriate buffer exchange step associated therewith. The results of the procedure of Example 2 are provided in Table 2 wherein the aggregate level ranges anywhere from as high as about 60% down to about 6% of aggregate by weight. Example 3 describes a pooling methodology which is applicable either to the Example 1, and flowchart 1 procedure or to the Example 2 and flowchart 2 procedure where RPHPLC is used as the analytical technique which is compared to a CE analytical technique. FIGS. 2, 3 and 4 show that RPHPLC is equivalent to CE. Example 4 provides preferred procedures for the CE analytical technique.

EMBODIMENTS OF THE INVENTION

1. A process for decreasing a level of aggregate of pegylated protein isoforms, said process comprising the steps of:
   (a) providing said pegylated protein isoforms; and
   (b) separating said pegylated protein isoforms by anion exchange chromatography using an anion exchange resin under sufficient conditions to decrease said level of said aggregate.
2. The process of embodiment 1 wherein said step (a) comprises the step of (a1) pegylating an unpegylated or a partially pegylated form of said protein, or pegylating both.
3. The process of embodiment 2 wherein said step (a1) comprises pegylating with free PEG selected from the group consisting of PEG-N-hydroxysuccinimide-5K, PEG-succinimidyl carbonate-5K, PEG-succinimidyl propionate-5K, PEG2-malemide-40K (2×20K), PEG2-N-hydroxysuccimide-40K (2×20K), and PEG2-aldehyde-40K (2×20K).
4. The process of embodiment 3 wherein a stoichiometric weight ratio of said free PEG to said unpegylated protein is from about 0.5 to about 100.
5. The process of embodiment 4 wherein said stoichiometric weight ratio is from about 1.5 to about 2.5.
6. The process of embodiment 5 wherein said stoichiometric weight ratio is from about 1.9 to about 2.
7. The process of embodiment 6 wherein said stoichiometric weight ratio is from about 1.95 to about 2.05.
8. The process of embodiment 2 wherein said pegylating step (a1) is conducted at a pegylating pH from about 3 to about 10.

9. The process of embodiment 8 wherein said pegylating pH is from about 7.2 to about 7.8.
10. The process of embodiment 9 wherein said pegylating pH is from about 7.4 to about 7.8.
11. The process of embodiment 10 wherein said pegylating pH is from about 7.40 to about 7.80.
12. The process of embodiment 2 wherein said pegylating step (a1) is conducted at a pegylating temperature is from about 0 to about 40° C.
13. The process of embodiment 12 wherein said pegylating temperature is from about 10 to about 30° C.
14. The process of embodiment 13 wherein said pegylating temperature is from about 18 to about 25° C.
15. The process of embodiment 1 further comprising an optional HIC step (a2) of selecting said pegylated protein by hydrophobic interaction chromatography (HIC) using an HIC resin.
16. The process of embodiment 2 further comprising an optional HIC step (a2) of selecting said pegylated protein by hydrophobic interaction chromatography (HIC) using an HIC resin.
17. The process of embodiment 16 wherein said HIC step (a2) comprises loading said pegylated protein and any unpegylated protein on said HIC resin at an HIC load of less than or equal to about 10 g protein/L of packed bed-volume of HIC resin.
18. The process of embodiment 17 wherein said HIC load is less than or equal to about 5 g protein/L of packed bed-volume of HIC resin.
19. The process of embodiment 18 wherein said HIC load is less than or equal to about 4.1 g protein/L of packed bed-volume of HIC resin.
20. The process of embodiment 17 wherein in said HIC step (a2) said loading is conducted at an HIC loading conductivity from about 30 to about 60 mS/cm.
21. The process of embodiment 20 wherein said HIC loading conductivity is from about 40 to about 52 mS/cm.
22. The process of embodiment 21 wherein said HIC loading conductivity is from about 45 to about 51 mS/cm.
23. The process of embodiment 17 wherein said HIC step (a2) is conducted at an HIC temperature from about 10 to about 40° C.
24. The process of embodiment 23 wherein said HIC temperature is from about 15 to about 30° C.
25. The process of embodiment 24 wherein said HIC temperature is from about 18 to about 25° C.
26. The process of embodiment 16 further comprising a UF/DF#3 step (a3) of ultrafiltering/diafiltering (UF/DF#3) of an eluent from said HIC step (a2).
27. The process of embodiment 26 wherein said UF/DF#3 step (a3) is conducted with a UF/DF#3 membrane having a UF/DF#3 membrane molecular weight cut-off (MWCO) from about 3 kDa to about 20 kDa.
28. The process of embodiment 27 wherein said UF/DF#3 membrane MWCO is from about 8 kDa to about 15 kDa.
29. The process of embodiment 28 wherein said UF/DF#3 membrane MWCO is from about 10 kDa to about 12 kDa.
30. The process of embodiment 29 wherein said UF/DF#3 membrane MWCO is about 10 kDa.
31. The process of embodiment 1 wherein said step (b) further comprises a step (b1) of loading said pegylated protein including any impurity and any aggregate thereof on said anion exchange (AEX) resin to provide loaded pegylated protein.
32. The process of embodiment 31 wherein said AEX resin is selected from the group consisting of ANX4, DEAE, Q-Sepharose, Q-Sepharose FF, Q Sepharose HP, and Q-Sepharose XL.
33. The process of embodiment 32 wherein said AEX resin is Q-Sepharose FF.
34. The process of embodiment 31 wherein said step (b1) is conducted at an AEX loading conductivity of less than or equal to about 10 mS/cm.
35. The process of embodiment 34 wherein said AEX loading conductivity is less than or equal to about 5 mS/cm.
36. The process of embodiment 35 wherein said AEX loading conductivity is less than or equal to about 2.4 mS/cm.
37. The process of embodiment 31 wherein said step (b1) is conducted at an AEX loading pH from about 5 to about 10.
38. The process of embodiment 37 wherein said AEX loading pH is from about 6.6 to about 9.
39. The process of embodiment 38 wherein said AEX loading pH is from about 6.9 to about 7.1.
40. The process of embodiment 31 wherein said step (b1) is conducted at an AEX load of pegylated protein including any impurity or said aggregate thereof of less than or equal to about 10 g protein/L of packed bed-volume of AEX resin.
41. The process of embodiment 40 wherein said AEX load is less than or equal to about 5.5 g protein/L of packed bed-volume of AEX resin.
42. The process of embodiment 40 wherein said AEX load is less than or equal to about 4.1 g protein/L of packed bed-volume of AEX resin.
43. The process of embodiment 1 wherein said pegylated protein comprises one or more of said pegylated protein isoforms PEG-1, PEG-2, PEG-3, PEG-4, PEG-5, PEG-6, PEG-7, PEG-8, and PEG-9 and any aggregate, trisulfide impurity and des-phe impurity thereof and any unpegylated impurity of said protein and any free PEG molecules.
44. The process of embodiment 1 wherein said pegylated protein comprises one or more of said pegylated protein isoforms PEG-2, PEG-3, PEG-4, PEG-5, PEG-6, PEG-7, PEG-8, and PEG-9 and any aggregate, trisulfide impurity and des-phe impurity thereof and any unpegylated impurity of said protein and any free PEG molecules.
45. The process of embodiment 1 wherein said pegylated protein comprises one or more of said pegylated protein isoforms PEG-2, PEG-3, PEG-4, PEG-5, PEG-6, PEG-7, PEG-8, and any aggregate, trisulfide impurity and des-phe impurity thereof and any unpegylated impurity of said protein and any free PEG molecules.
46. The process of embodiment 1 wherein said pegylated protein comprises one or more of said pegylated protein isoforms PEG-3, PEG-4, PEG-5, PEG-6, PEG-7, PEG-8, and any aggregate, trisulfide impurity and des-phe impurity thereof and any unpegylated impurity of said protein and any free PEG molecules.
47. The process of embodiment 1 wherein said pegylated protein comprises one or more of said pegylated protein isoforms PEG-4, PEG-5, PEG-6, PEG-7, PEG-8, and any aggregate and trisulfide and des-phe impurities thereof and any unpegylated impurity of said protein and any free PEG molecules.
48. The process of embodiment 1 wherein said pegylated protein comprises one or more of said pegylated protein isoforms PEG-4, PEG-5, PEG-6, PEG-7 and any aggregate, trisulfide impurity and des-phe impurity thereof and any unpegylated impurity of said protein and any free PEG molecules.

49. The process of embodiment 1 wherein said pegylated protein comprises one or more of said pegylated protein isoforms PEG-4, PEG-5, PEG-6 and any aggregate, trisulfide impurity and des-phe impurity thereof and any unpegylated impurity of said protein and any free PEG molecules.

50. The process of embodiment 1 wherein said pegylated protein comprises one or more of said pegylated protein isoforms PEG-4, PEG-5, PEG-6 and any aggregate, trisulfide impurity and des-phe impurity thereof and any unpegylated impurity of said protein.

51. The process of embodiment 1 wherein said pegylated protein comprises one or more of said pegylated protein isoforms PEG-1, PEG-2, PEG-3, PEG-4, PEG-5, PEG-6, PEG-7, PEG-8, and PEG-9 and any aggregate, trisulfide impurity and des-phe impurity thereof.

52. The process of embodiment 1 wherein said pegylated protein comprises one or more of said pegylated protein isoforms PEG-1, PEG-2, PEG-3, PEG-4, PEG-5, PEG-6, PEG-7, PEG-8, and PEG-9 and any aggregate and trisulfide impurity thereof.

53. The process of embodiment 1 wherein said pegylated protein comprises one or more of said pegylated protein isoforms PEG-1, PEG-2, PEG-3, PEG-4, PEG-5, PEG-6, PEG-7, PEG-8, and PEG-9 and any aggregate thereof.

54. The process of embodiment 1 further comprising a pooling step (c) of pooling discrete amounts of said pegylated protein isoforms to yield a pooled pegylated protein by a technique selected from the group consisting of capillary electrophoresis (CE), sodium dodecyl sulfate-polyacrylamide gel electrophoresis (SDS-PAGE), ion exchange (IEX) chromatography, hydrophobic interaction chromatography (HIC), anion exchange (AEX) chromatography, cation exchange (CEX) chromatography, reverse-phase high pressure liquid chromatography (RPHPLC), size exclusion high pressure liquid chromatography (SEHPLC), affinity chromatography (AC) and combinations thereof.

55. The process of embodiment 42 further comprising a pooling step (c) of pooling discrete amounts of said pegylated protein isoforms of said pegylated protein to yield a pooled pegylated protein by a technique selected from the group consisting of capillary electrophoresis (CE), sodium dodecyl sulfate-polyacrylamide gel electrophoresis (SDS-PAGE), ion exchange (IEX) chromatography, hydrophobic interaction chromatography (HIC), anion exchange (AEX) chromatography, cation exchange (CEX) chromatography, reverse-phase high pressure liquid chromatography (HPLC), size exclusion high pressure liquid chromatography (SEHPLC), and affinity chromatography (AC) and combinations thereof.

56. The process of embodiment 54 wherein said pooling step (c) is conducted by said CE at a CE temperature from about 5 to about 50° C.

57. The process of embodiment 55 wherein said pooling step 9c) is conducted by said CE at a CE temperature from about 5 to about 50° C.

58. The process of embodiment 56 wherein said CE temperature is from about 5 to about 45° C.

59. The process of embodiment 58 wherein said CE temperature is from about 20 to about 40° C.

60. The process of embodiment 59 wherein said CE temperature is from about 30 to about 32° C.

61. The process of embodiment 56 wherein said pooling step (c) is conducted by said CE at a CE pooling conductivity from about 0 to about 60 mS/cm.

62. The process of embodiment 61 wherein said CE pooling conductivity is from about 5 to about 10 mS/cm.

63. The process of embodiment 54 wherein said pooling step (c) is conducted on said pegylated protein isoforms provided in a buffer at a protein concentration of at least about 0.2 mg/ml.

64. The process of embodiment 56 wherein said pooling step (c) is conducted on said pegylated protein isoforms provided in a buffer at a protein concentration of at least about 0.5 mg/ml.

65. The process of embodiment 54 wherein said pooling step (c) is conducted on said pegylated protein isoforms provided in a buffer at a protein concentration from about 0.1 to about 100 mg/ml.

66. The process of embodiment 65 wherein said protein concentration is from about 0.5 to about 10 mg/ml.

67. The process of embodiment 66 wherein said protein concentration is from about 2 to about 3 mg/ml.

68. The process of embodiment 56 wherein said pooling step (c) is conducted on said pegylated protein isoforms provided in a buffer at a protein concentration from about 0.1 to about 100 mg/ml.

69. The process of embodiment 67 wherein said protein concentration is from about 0.5 to about 10 mg/ml.

70. The process of embodiment 68 wherein said protein concentration is from about 2 to about 3 mg/ml.

71. The process of embodiment 63 wherein said pooled pegylated protein comprises one or more of PEG-1, PEG-2, PEG-3, PEG-4, PEG-5, PEG-6, PEG-7, PEG-8, and PEG-9.

72. The process of embodiment 63 wherein said pooled pegylated protein comprises one or more of PEG-2, PEG-3, PEG-4, PEG-5, PEG-6, PEG-7, PEG-8, and PEG-9.

73. The process of embodiment 63 wherein said pooled pegylated protein comprises one or more of PEG-3, PEG-4, PEG-5, PEG-6, PEG-7, PEG-8, and PEG-9.

74. The process of embodiment 63 wherein said pooled pegylated protein comprises one or more of PEG-3, PEG-4, PEG-5, PEG-6, PEG-7, and PEG-8.

75. The process of embodiment 63 wherein said pooled pegylated protein comprises one or more of PEG-3, PEG-4, PEG-5, PEG-6, and PEG-7.

76. The process of embodiment 63 wherein said pooled pegylated protein comprises one or more of PEG-3, PEG-4, PEG-5, and PEG-6.

77. The process of embodiment 63 wherein said pooled pegylated protein comprises one or more of PEG-4, PEG-5, and PEG-6.

78. The process of embodiment 63 wherein said pooled pegylated protein comprises one or more of PEG-4 and PEG-5.

79. The process of embodiment 63 wherein said pooled pegylated protein comprises one or more of PEG-S, and PEG-6.

80. The process of embodiment 63 wherein said pooled pegylated protein comprises PEG-5.

81. The process of embodiment 71 wherein a pooled pegylated protein fraction of PEG-4, PEG-5 and PEG-6 comprises at least about 70% by weight based on a total weight of said PEG-1, PEG-2, PEG-3, PEG-4, PEG-5, PEG-6, PEG-7, PEG-8 and PEG-9 pegylated protein isoforms and any aggregate thereof.

82. The process of embodiment 71 wherein said pooled pegylated protein fraction of PEG-4, PEG-5 and PEG-6 comprises at least about 75% by weight based on a total weight of said PEG-1, PEG-2, PEG-3, PEG-4, PEG-5, PEG-6, PEG-7, PEG-8 and PEG-9 pegylated protein isoforms and any aggregate thereof.

83. The process of embodiment 71 wherein said pooled pegylated protein fraction of PEG-4, PEG-5 and PEG-6 comprises at least about 80% by weight based on a total weight of said PEG-1, PEG-2, PEG-3, PEG-4, PEG-5, PEG-6, PEG-7, PEG-8 and PEG-9 pegylated protein isoforms and any aggregate thereof.

84. The process of embodiment 71 wherein said pooled pegylated protein fraction of PEG-4, PEG-5 and PEG-6 comprises at least about 90% by weight based on a total weight of said PEG-1, PEG-2, PEG-3, PEG-4, PEG-5, PEG-6, PEG-7, PEG-8 and PEG-9 pegylated protein isoforms and any aggregate thereof.

85. The process of embodiment 71 wherein said pooled pegylated protein fraction of PEG-4, PEG-5 and PEG-6 comprises at least about 94% by weight based on a total weight of said PEG-1, PEG-2, PEG-3, PEG-4, PEG-5, PEG-6, PEG-7, PEG-8 and PEG-9 pegylated protein isoforms and any aggregate thereof.

86. The process of embodiment 64 wherein said buffer in which said pegylated protein is provided has a pH from about 5 to about 10.

87. The process of embodiment 86 wherein said buffer has a pH from about 6.6 to about 9.

88. The process of embodiment 87 wherein said buffer has a pH from about 6.9 to about 7.1.

89. The process of embodiment 64 wherein said buffer in which said pegylated protein is provided is selected from the group consisting of Tris, phosphate, HEPES, citric acid, triethylamine, and histidine.

90. The process of embodiment 1 wherein said level of said aggregate is less than or equal to about 10% by weight based on a total weight of said isoforms and said aggregate.

91. The process of embodiment 90 wherein said level of said aggregate is less than or equal to about 9% by weight based on said total weight.

92. The process of embodiment 91 wherein said level of said aggregate is less than or equal to about 8% by weight based on said total weight.

93. The process of embodiment 92 wherein said level of said aggregate is less than or equal to about 7% by weight based on said total weight.

94. The process of embodiment 93 wherein said level of said aggregate is less than or equal to about 6% by weight based on said total weight.

95. The process of embodiment 94 wherein said level of said aggregate is less than or equal to about 5% by weight based on said total weight.

96. The process of embodiment 95 wherein said level of said aggregate is less than or equal to about 4% by weight based on said total weight.

97. The process of embodiment 96 wherein said level of said aggregate is less than or equal to about 3% by weight based on said total weight.

98. The process of embodiment 97 wherein said level of said aggregate is less than or equal to about 2% by weight based on said total weight.

99. The process of embodiment 98 wherein said level of said aggregate is less than or equal to about 1.5% by weight based on said total weight.

100. The process of embodiment 99 wherein said level of said aggregate is less than or equal to about 1% by weight based on said total weight.

101. The process of embodiment 100 wherein said level of said aggregate is less than or equal to about 0.9% by weight based on said total weight.

102. The process of embodiment 101 wherein said level of said aggregate is less than or equal to about 0.8% by weight based on said total weight.

103. The process of embodiment 102 wherein said level of said aggregate is less than or equal to about 0.7% by weight based on said total weight.

104. The process of embodiment 103 wherein said level of said aggregate is less than or equal to about 0.6% by weight based on said total weight.

105. The process of embodiment 104 wherein said level of said aggregate is less than or equal to about 0.5% by weight based on said total weight.

106. The process of embodiment 105 wherein said level of said aggregate is less than or equal to about 0.4% by weight based on said total weight.

107. The process of embodiment 106 wherein said level of said aggregate is less than or equal to about 0.3% by weight based on said total weight.

108. The process of embodiment 107 wherein said level of said aggregate is less than or equal to about 0.2% by weight based on said total weight.

109. The process of embodiment 108 wherein said level of said aggregate is less than or equal to about 0.1% by weight based on said total weight.

110. The process of embodiment 109 wherein said level of said aggregate is less than or equal to about 0.05% by weight based on said total weight.

111. The process of embodiment 110 wherein said level of said aggregate is less than or equal to about 0.01% by weight based on said total weight.

112. The process of embodiment 31 wherein said step (b) further comprises a step (b2) of washing said loaded pegylated protein followed by a step (b3) of eluting with an eluting solution said loaded pegylated protein by a pH gradient or an ionic strength gradient and a step (b4) of collecting an eluent in multiple volume fractions.

113. The process of embodiment 31 wherein said step (b) further comprises a step (b2) of washing said loaded pegylated protein followed by an eluting step (b3) of eluting said loaded pegylated protein with a salt solution in an eluting buffer containing an ionic salt at a salt concentration gradient sufficient to elute said loaded pegylated protein from said AEX resin.

114. The process of embodiment 113 wherein said ionic salt is a chloride salt.

115. The process of embodiment 114 wherein said ionic salt is NaCl.

116. The process of embodiment 115 wherein said step (b) is conducted in a column having a column volume (CV) and wherein said salt concentration gradient is from about 2 to about 50 mM per CV.

117. The process of embodiment 116 wherein said salt concentration gradient is from about 5 to about 25 mM per CV.

118. The process of embodiment 117 wherein said salt concentration gradient is from about 10 to about 20 mM per CV.

119. The process of embodiment 113 wherein said eluting buffer has a pH from about 5 to about 10.

120. The process of embodiment 119 wherein said eluting buffer has a pH from about 6.6 to about 9.

121. The process of embodiment 120 wherein said eluting buffer has a pH from about 6.9 to about 7.1.

122. The process of embodiment 113 wherein said eluting step (b3) is conducted at an eluting temperature of less than or equal to 50° C.

123. The process of embodiment 122 wherein said eluting temperature is less than or equal to about 35° C.

124. The process of embodiment 123 wherein said eluting temperature is from about 2 to about 30° C.
125. The process of embodiment 123 wherein said eluting temperature is from about 15 to about 30° C.
126. The process of embodiment 123 wherein said eluting temperature is from about 18 to about 25° C.
127. The process of embodiment 113 wherein said step (b) is conducted in a column and wherein said eluting buffer has a linear velocity through said column of less than or equal to about 300 cm/hr.
128. The process of embodiment 127 wherein said linear velocity is from about 10 to about 150 cm/hr.
129. The process of embodiment 127 wherein said linear velocity is from about 30 to about 150 cm/hr.
130. The process of embodiment 127 wherein said linear velocity is from about 50 to about 100 cm/hr.
131. The process of embodiment 127 wherein said linear velocity is from about 50 to about 70 cm/hr.
132. The process of embodiment 127 wherein said linear velocity is from about 60 to about 65 cm/hr.
133. The process of embodiment 127 wherein said linear velocity is about 60 cm/hr.
134. The process of embodiment 1 wherein said pegylated protein is selected from the group consisting of hormone, growth hormone, human growth hormone, growth hormone antagonist, human growth hormone antagonist, an antibody, and B-2036 PEG.
135. The process of embodiment 1 wherein said anion exchange (AEX) resin comprises functional groups selected from the group consisting of primary, secondary, tertiary, quaternary amines, and combinations thereof.
136. The process of embodiment 1 wherein said anion exchange (AEX) resin comprises functional groups selected from the group consisting of diethylaminoethyl, diethylaminopropyl, dimethylethanolamine, trimethylammonium-ethyl, trimethylbenzyl ammonium, dimethylethanol benzyl and polyamine functional groups.
137. The process of embodiment 1 wherein said anion exchange (AEX) resin comprises a support material selected from the group consisting of hydrophilic polyether, crosslinked divinyl benzene polystyrene, crosslinked agarose, polypropylene, hydrophilic acrylamidovinyl, methacrylic, polymerized hydrogel with a ceramic bead base, composite silica-dextran material, polymer grafted silica, divinyl benzene styrene, divinyl benzene polyacrylic, crosslinked cellulose, co-polymer methacrylate, polystyrene, acrylic, G5000 hydrophilic gel, and cellulose.
138. The process of embodiment 1 wherein said anion exchange (AEX) resin comprises a macroporous resin.
139. The process of embodiment 1 wherein said anion exchange (AEX) resin comprises a gel resin.
140. The process of embodiment 63 wherein said pooled pegylated protein consists essentially of one or more of PEG-1, PEG-2, PEG-3, PEG-4, PEG-5, PEG-6, PEG-7, PEG-8, and PEG-9.
141. The process of embodiment 63 wherein said pooled pegylated protein consists essentially of one or more of PEG-2, PEG-3, PEG-4, PEG-5, PEG-6, PEG-7, PEG-8, and PEG-9.
142. The process of embodiment 63 wherein said pooled pegylated protein consists essentially of one or more of PEG-3, PEG-4, PEG-5, PEG-6, PEG-7, PEG-8, and PEG-9.
143. The process of embodiment 63 wherein said pooled pegylated protein consists essentially of one or more of PEG-3, PEG-4, PEG-5, PEG-6, PEG-7, and PEG-8.
144. The process of embodiment 63 wherein said pooled pegylated protein consists essentially of one or more of PEG-3, PEG-4, PEG-5, PEG-6, and PEG-7.
145. The process of embodiment 63 wherein said pooled pegylated protein consists essentially of one or more of PEG-3, PEG-4, PEG-5, and PEG-6.
146. The process of embodiment 63 wherein said pooled pegylated protein consists essentially of one or more of PEG-4, PEG-5, and PEG-6.
147. The process of embodiment 63 wherein said pooled pegylated protein consists essentially of one or more of PEG-4 and PEG-5.
148. The process of embodiment 63 wherein said pooled pegylated protein consists essentially of one or more of PEG-5, and PEG-6.
149. The process of embodiment 63 wherein said pooled pegylated protein consists essentially of PEG-5.
150. The process of embodiment 31 wherein said step (b) is conducted in a column having a column volume (CV) and wherein said step (b) further comprises a step (b2) of washing said loaded pegylated protein followed by a step (b3) of eluting with an eluting solution said loaded pegylated protein by a pH gradient or an ionic strength gradient and a step (b4) of collecting an eluent in multiple volume fractions from about 0.1 to about 5 of said column volume (CV).
151. The process of embodiment 31 wherein said step (b) is conducted in a column having a column volume (CV) and wherein said step (b) further comprises a step (b2) of washing said loaded pegylated protein followed by a step (b3) of eluting with an eluting solution said loaded pegylated protein by a pH gradient or an ionic strength gradient and a step (b4) of collecting an eluent in multiple volume fractions from about 0.1 to about 1 of said column volume (CV).
152. The process of embodiment 31 wherein said step (b) is conducted in a column having a column volume (CV) and wherein said step (b) further comprises a step (b2) of washing said loaded pegylated protein followed by a step (b3) of eluting with an eluting solution said loaded pegylated protein by a pH gradient or an ionic strength gradient and a step (b4) of collecting an eluent in multiple volume fractions from about 0.1 to about 0.5 of said column volume (CV).
153. The process of embodiment 31 wherein said step (b) is conducted in a column having a column volume (CV) and wherein said step (b) further comprises a step (b2) of washing said loaded pegylated protein followed by a step (b3) of eluting with an eluting solution said loaded pegylated protein by a pH gradient or an ionic strength gradient and a step (b4) of collecting an eluent in multiple volume fractions from about 0.1 to about 0.2 of said column volume (CV).
154. The process of embodiment 113 wherein said ionic salt is selected from the group consisting of NaCl, lithium chloride, Na phosphate, Na sulfate, ammonium chloride, ammonium sulfate, ammonium phosphate, KI, and KCl.
155. The process of embodiment 118 wherein said salt concentration gradient is from about 10 to about 12.5 mM per CV.
156. A process for pooling pegylated protein isoforms, said process comprising the step of:
(a) separating and collecting said pegylated protein isoforms by a technique selected from the group consisting of capillary electrophoresis (CE), sodium dodecyl sulfate-polyacrylamide gel electrophoresis (SDS-PAGE), ion exchange (IEX) chromatography, hydrophobic interaction chromatography (HIC), anion exchange (AEX) chromatography, cation exchange (CEX) chromatography, reverse-phase high pressure liquid chromatography (RPHPLC), size exclusion high pressure liquid chromatography (SEHPLC), affinity chromatography and combinations thereof.

157. The process of embodiment 140 when said technique is RPHPLC or CE.

158. A process for decreasing a level of aggregate of pegylated growth hormone antagonist isoforms having a total weight of said isoforms and said aggregate, said process comprising the steps of:
   (a) providing said pegylated growth hormone antagonist isoforms; and
   (b) separating said pegylated growth hormone antagonist isoforms on an anion exchange (AEX) resin by anion exchange chromatography under sufficient conditions to decrease said level of said aggregate to less than or equal to about 6% by weight based on said total weight.

159. The process of embodiment 158 wherein the conditions are sufficient to decrease said level of said aggregate to less than or equal to about 5% by weight based on said total weight.

160. The process of embodiment 158 wherein the conditions are sufficient to decrease said level of said aggregate to less than or equal to about 4% by weight based on said total weight.

161. The process of embodiment 158 wherein the conditions are sufficient to decrease said level of said aggregate to less than or equal to about 3% by weight based on said total weight.

162. The process of embodiment 158 wherein the conditions are sufficient to decrease said level of said aggregate to less than or equal to about 2% by weight based on said total weight.

163. The process of embodiment 158 wherein the conditions are sufficient to decrease said level of said aggregate to less than or equal to about 1% by weight based on said total weight.

164. A process for decreasing a total level of a sum of any trisulfide impurity, any des-phe impurity and any aggregate of pegylated growth hormone antagonist isoforms having a total weight of said isoforms, said impurities and said aggregate, said process comprising the steps of:
   (a) providing said pegylated growth hormone antagonist isoforms; and
   (b) separating said pegylated growth hormone antagonist isoforms on an anion exchange (AEX) resin by anion exchange chromatography under sufficient conditions to decrease said total level of any said trisulfide impurity, any of said des-phe impurity and any of said aggregate to less than or equal to about 15% by weight based on said total weight.

165. The process of embodiment 164 wherein the conditions are sufficient to decrease said total level of any said trisulfide impurity, any of said des-phe impurity and any of said aggregate to less than or equal to about 12% by weight based on said total weight.

166. The process of embodiment 164 wherein the conditions are sufficient to decrease said total level of any said trisulfide impurity, any of said des-phe impurity and any of said aggregate to less than or equal to about 10% by weight based on said total weight.

167. The process of embodiment 164 wherein the conditions are sufficient to decrease said total level of any said trisulfide impurity, any of said des-phe impurity and any of said aggregate to less than or equal to about 9% by weight based on said total weight.

168. The process of embodiment 164 wherein the conditions are sufficient to decrease said total level of any said trisulfide impurity, any of said des-phe impurity and any of said aggregate to less than or equal to about 8% by weight based on said total weight.

169. The process of embodiment 164 wherein the conditions are sufficient to decrease said total level of any said trisulfide impurity, any of said des-phe impurity and any of said aggregate to less than or equal to about 7% by weight based on said total weight.

170. The process of embodiment 164 wherein the conditions are sufficient to decrease said total level of any said trisulfide impurity, any of said des-phe impurity and any of said aggregate to less than or equal to about 6% by weight based on said total weight.

171. The process of embodiment 164 wherein the conditions are sufficient to decrease said total level of any said trisulfide impurity, any of said des-phe impurity and any of said aggregate to less than or equal to about 5% by weight based on said total weight.

172. The process of embodiment 164 wherein the conditions are sufficient to decrease said total level of any said trisulfide impurity, any of said des-phe impurity and any of said aggregate to less than or equal to about 4% by weight based on said total weight.

173. The process of embodiment 164 wherein the conditions are sufficient to decrease said total level of any said trisulfide impurity, any of said des-phe impurity and any of said aggregate to less than or equal to about 3% by weight based on said total weight.

174. The process of embodiment 164 wherein the conditions are sufficient to decrease said total level of any said trisulfide impurity, any of said des-phe impurity and any of said aggregate to less than or equal to about 2% by weight based on said total weight.

175. The process of embodiment 164 wherein the conditions are sufficient to decrease said total level of any said trisulfide impurity, any of said des-phe impurity and any of said aggregate to less than or equal to about 1% by weight based on said total weight.

176. The process of embodiment 134 wherein said growth hormone antagonist is B-2036 PEG wherein said B-2036 PEG comprises a growth hormone antagonist polypeptide backbone of B-2036 of [SEQ. ID NO. 1].

177. The process of embodiment 134 wherein said growth hormone is a pegylated form of a polypeptide of [SEQ. ID NO. 2].

178. The process of embodiment 137 wherein said support material has a diameter from about 10 to about 500 μm.

179. The process of embodiment 178 wherein said diameter has an average of 90 μm.

180. A process for pooling pegylated protein isoforms, said process comprising the steps of:
   (a) separating said pegylated protein isoforms into selected isoforms; and
   (b) combining said selected isoforms to yield an enriched pool of said selected isoforms.

181. The process of embodiment 180 wherein said selected isoforms are PEG-4, PEG-5 and PEG-6 with a pool weight ratio of ((a first weight of PEG-4+PEG-5+PEG-6)/(a second weight of any PEG-I+PEG-2+PEG-3+PEG-4+PEG-5+PEG-6+PEG-7+PEG-8+PEG-9 present in said enriched pool)) which pool weight ratio is greater than or equal to about 70% by weight.

182. The process of embodiment 181 wherein said pool weight ratio is greater than or equal to about 75% by weight.
183. The process of embodiment 181 wherein said pool weight ratio is greater than or equal to about 80% by weight.
184. The process of embodiment 181 wherein said pool weight ratio is greater than or equal to about 85% by weight.
185. The process of embodiment 181 wherein said pool weight ratio is greater than or equal to about 90% by weight.
186. The process of embodiment 181 wherein said pool weight ratio is greater than or equal to about 94% by weight.
187. The process of embodiment 181 wherein said pool weight ratio is greater than or equal to about 95% by weight.
188. The process of embodiment 181 wherein said pool weight ratio is greater than or equal to about 96% by weight.
189. The process of embodiment 181 wherein said pool weight ratio is greater than or equal to about 97% by weight.
190. The process of embodiment 181 wherein said pool weight ratio is greater than or equal to about 98% by weight.
191. The process of embodiment 181 wherein said pool weight ratio is greater than or equal to about 99% by weight.
192. The process of embodiment 181 wherein said pool weight ratio is greater than or equal to about 99.5% by weight.
193. The process of embodiment 181 wherein said pool weight ratio is greater than or equal to about 99.9% by weight.
194. The process of embodiment 180 wherein said selected isoforms are one or more of PEG-1, PEG-2, PEG-3, PEG-4, PEG-5, PEG-6, PEG-7, PEG-8, and PEG-9.
195. The process of embodiment 180 wherein said selected isoforms are one or more of PEG-2, PEG-3, PEG-4, PEG-5, PEG-6, PEG-7, PEG-8, and PEG-9.
196. The process of embodiment 180 wherein said selected isoforms are one or more of PEG-3, PEG-4, PEG-5, PEG-6, PEG-7, PEG-8, and PEG-9.
197. The process of embodiment 180 wherein said selected isoforms are one or more of PEG-4, PEG-5, PEG-6, PEG-7, PEG-8, and PEG-9.
198. The process of embodiment 180 wherein said selected isoforms are one or more of PEG-4, PEG-5, PEG-6, PEG-7, and PEG-8.
199. The process of embodiment 180 wherein said selected isoforms are one or more of PEG-4, PEG-5, PEG-6 and PEG-7.
200. The process of embodiment 180 wherein said selected isoforms are one or more of PEG-4, PEG-5, and PEG-6.
201. The process of embodiment 180 wherein said selected isoforms are one or more of PEG-4 and PEG-5.
202. The process of embodiment 180 wherein said selected isoforms are one or more of PEG-5, and PEG-6.
203. The process of embodiment 180 wherein said selected isoforms are one or more of PEG-4 and PEG-6.
204. A process for obtaining a selected pegylated protein isoform from a mixture of at least two pegylated protein isoforms, said process comprising the step of:
  (a) separating said selected pegylated protein isoform from said mixture.
205. A process for preparing an enriched composition from a starting composition, wherein said starting composition comprises unpegylated B-2036 and one or more pegylated isoforms of B-2036 selected from the group consisting of PEG-1, PEG-2, PEG-3, PEG-4, PEG-5, PEG-6, PEG-7, PEG-8, and PEG-9, and wherein said process comprises the steps of:
  (a) separating said starting composition into a plurality of fractions, wherein a first fraction weight ratio of PEG-4, PEG-5, and PEG-6 isoforms to total unpegylated B-2036 and pegylated B-2036 isoforms in at least one fraction differs from a second fraction weight ratio of PEG-4, PEG-5, and PEG-6 isoforms to total unpegylated B-2036 and pegylated B-2036 isoforms in at least one other fraction,
  (b) determining a weight ratio of PEG-4, PEG-5, and PEG-6 isoforms to total unpegylated B-2036 and pegylated B-2036 isoforms of a remainder of each fraction or in a sampling of fractions, and
  (c) selectively combining less than all of said fractions to yield said enriched composition, wherein an enriched fraction weight ratio of PEG-4, PEG-5, and PEG-6 isoforms to total unpegylated B-2036 and pegylated B-2036 isoforms is greater in said enriched composition than in said starting composition.

All numerical values and identified molecules in this application are exemplary and are not intended to be construed as claim limiting. The following is presented by way of example and is not to be construed as a limitation to the scope of the invention. All citations to books, magazines, journal articles, patents, or any other publications, etc., recited in this application are expressly incorporated herein by reference in their entirety for all purposes.

EXAMPLES

Example 1

Maintain or Decrease Level of Aggregate of Pegylated Growth Hormone Antagonist (B-2036-PEG) by Anion Exchange Chromatography Maintenance (below a desired level—e.g., ≦6% by weight of total weight) or decrease of aggregate levels of B-2036 PEG was accomplished by using BI (the Bulk Intermediate B-2036) as the starting material prepared as indicated in non-provisional U.S. patent application Ser. No. 10/662,884 entitled Method for the Production Of Growth Hormone And Antagonist Thereof Having Lower Levels Of Isoform Impurities Thereof, filed Sep. 16, 2003 before the U.S. Patent and Trademark Office. Fermentation (to yield B-2036) in a recombinant *E. coli* expression system was carried out as described by Cunningham et al. in U.S. Pat. No. 5,849,535. Purification of B-2036 BI was performed as described by the above-identified non-provisional U.S. patent application Ser. No. 10/662,884). This material was then processed using the initial pegylation and hydrophobic interaction chromatography steps as noted in flowchart 1 below to produce B-2036 PEG. Following the hydrophobic interaction chromatography (step 2), the B-2036 PEG was UF/DF into pH 7, 25 mM TRIS buffer (instead of pH 4 sodium acetate buffer as in the process of Example 2, step 3, flowchart 2). The retentate was then subjected to Q Sepharose FF column strong anion exchange chromatography. This step separates differentially PEGylated species into fractions for pooling to achieve the PEGylated species distribution required for API release. This column enriches for the PEG-4, PEG-5 and PEG-6 products of PEGylated BI (B-2036 PEG). The product is eluted with a 20 CV linear gradient from 0-250 mM NaCl in 25 mM Tris, pH 7.0 following equilibration steps and a 2 CV wash with 25 mM Tris, pH 7.0. Analysis of fractions is accomplished using CE instead of SDS-PAGE as noted in Example 2, flowchart 2. See previous discussion regarding same. Pegvisomant (Somavert®; Pharmacia) is collected from the chromatography profile as a pool from fractions analyzed by CE with a pooling criteria of >75% PEG4+5+6 (first fraction) and >94% PEG4+5+6 (last fraction) and >0.5 mg/mL. The resulting product was then carried through the remainder of the B-2036 PEG purification process as described in flowchart 1. After selection and pooling of the fractions, the analysis of the pooled material and final API by SEHPLC showed no detectable aggregate. See Table 1 indicating the same below.

FLOWCHART 1
Example 1
(Process Using Anion Exchange Resin)

| UNIT OPERATION | PROCESS DESCRIPTION AND CONTROL | PROCESS CONTROLS |
|---|---|---|
| 1. Pegylation | The B-2036 from the purified BI process is PEGylated with a 2 g/g excess of the PEGylation reagent, N-hydroxysuccinimidyl ester of methoxy(polyethylene glycol) propionic acid, MW 5,000 (m-SPA-5000) in 100 mM Hepes, pH 7.65. The PEGylated product is reacted in a stainless steel tank by the addition of solid PEG with stirring for 60-90 min.<br><br>pH = 7.65 in B-2036 UF/DF #2 buffer | API Step Range / Manf. Spec. / Demonstrated Acceptable<br><br>PEGylation<br>1. Temperature<br>  – low & high    18-25°C    15-28.9°C<br>2. pH<br>  – low & high    7.40-7.80    7.20-8.00<br>3. BI concentration    9.3 g/L    9-10 g/L |
| ↓ Pegylated B-2036 ↓ | | |
| 2. Hydrophobic Interaction Chromatography (optional step) | The PEGylation reaction mixture is conditioned for hydrophobic interaction chromatography dilution (1:1) with 800 mM sodium citrate, 50 mM Tris, pH 7.6. The product is loaded onto the Phenyl column, washed with 400 mM sodium citrate, 50 mM Tris, pH 7.5, and product is collected by reverse salt gradient from 400 mM sodium citrate, 50 mM Tris, pH 7.5 to 50 mM Tris, pH 7.7 and fractions are collected when protein is detected by UV spectroscopy (e.g., the UV increases during elution).<br><br>Resin type:   TosoHaas Toyopearl Phenyl 650M resin<br>Phenyl load:   1:1 of PEGylation pool with buffer<br>Flow rate:   60 cm/hr | Toyopearl Phenyl 650M<br>API Step Range / Manf. Spec. / Demonstrated Acceptable<br><br>1. Load capacity    </= 4.1 g/L resin    ≤ 5 g/L<br>2. Gradient slope    4+/-0.06 CV    3.88-4.12<br>3. Load conductivity    45-51 mS/cm    40-51 mS/cm<br><br>Column end equil conductivity    40-51 mS/cm |

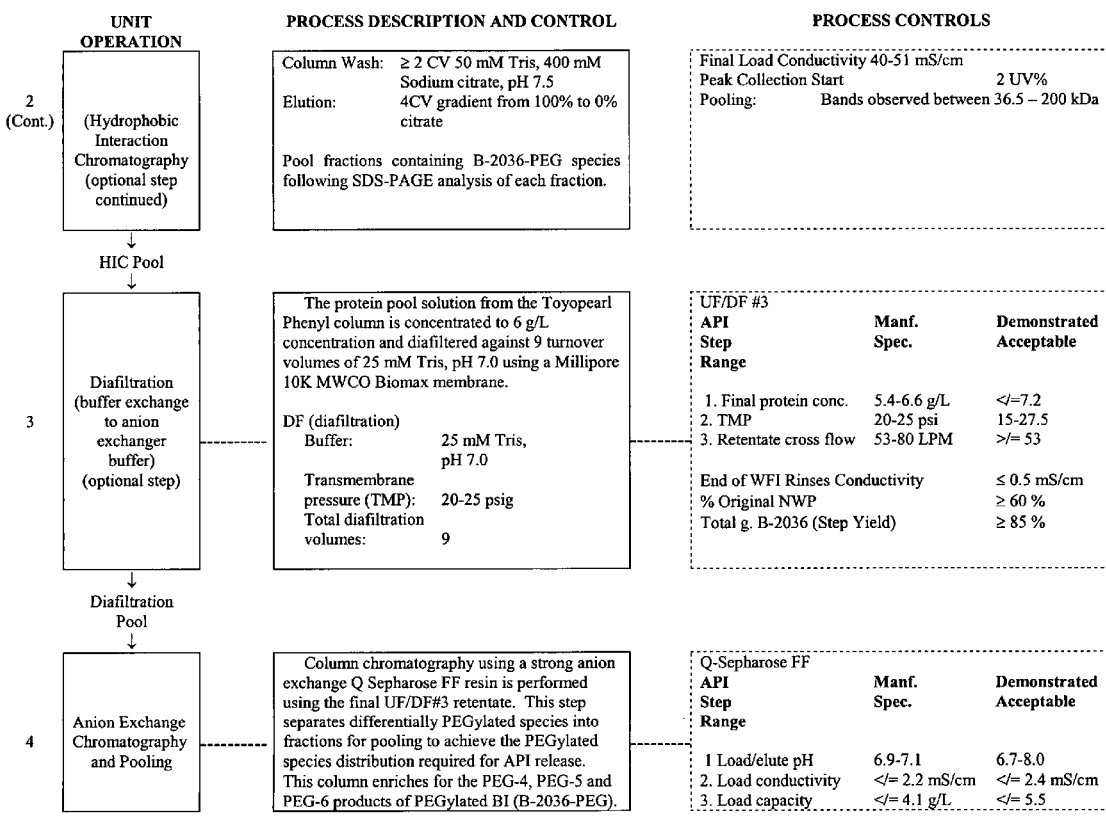

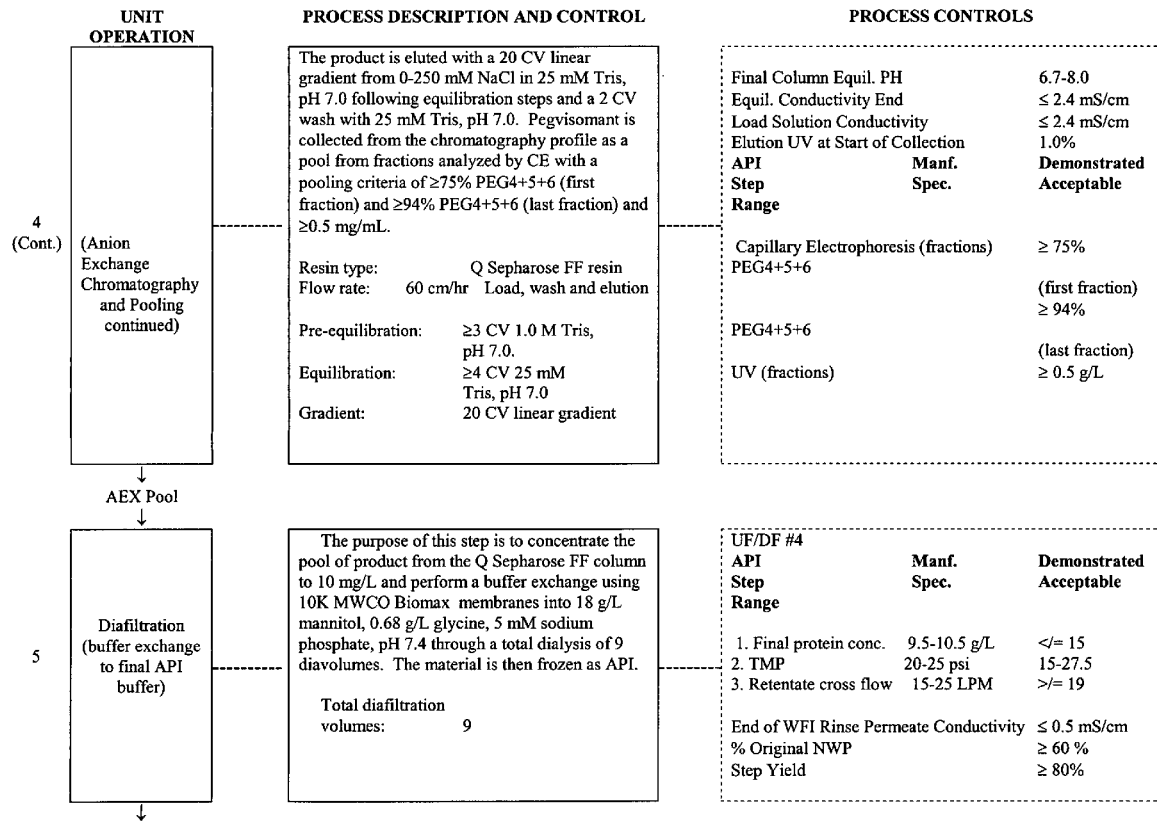

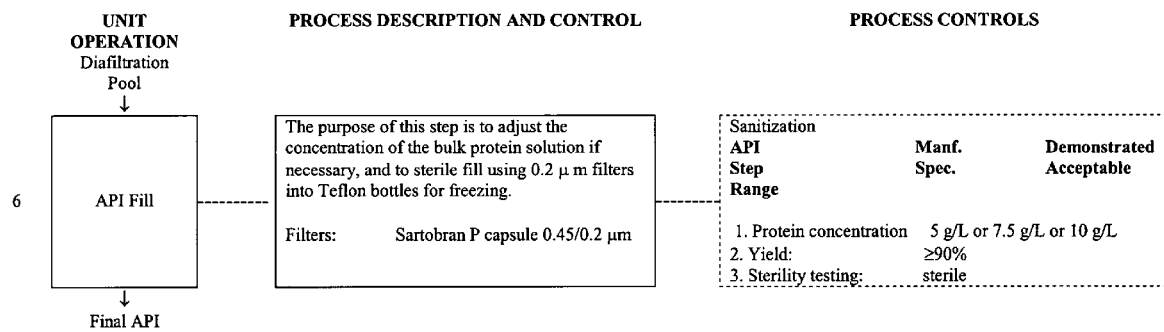

The following data was obtained using the above-noted procedure of Example 1.

TABLE 1

Anion Exchange Chromatography Parameters and Yield with Aggregate Data

| Resin | pH Equilibrate | Load | Elute | Gradient buffer A | buffer B | Slope (CV) | Bed Ht. .6 cm col. (cm) | Load (mg/mL resin) | In-process analytical | Yield (%) | % Aggregate | Av. PEG No.* |
|---|---|---|---|---|---|---|---|---|---|---|---|---|
| ANX4FF | 8.0 | 8.0 | 6.7 | 25 mM Tris pH 8.0 | 25 mM Tris, 90 mM NaCl, pH 6.7 | 15 | 20 | 5.1 | pooled by SDS-PAGE | 50 | 0 | N/A |
| ANX4FF (40 mL CV) | 8.0 | 8.0 | 6.7 | 25 mM Tris pH 8.0 | 25 mM Tris, 90 mM NaCl, pH 6.7 | 15 | 20 | 5.1 | pooled by SDS-PAGE | 54.7 | 0 | N/A |
| Q Sepharose FF | 8.0 | 8.0 | 6.7 | 25 mM Tris pH 8.0 | 25 mM Tris, 150 mM NaCl, pH 6.7 | 20 | 20 | 3.6 | pooled by SDS-PAGE/1st use of CE | 65.8 | 0 | 5.7 |
| Q Sepharose FF | 8.0 (add 3CV 1M Tris, pH 8.0 pre-equil step) | 8.0 | 6.7 | 25 mM Tris pH 8.0 | 25 mM Tris, 150 mM NaCl, pH 6.7 | 20 | 20 | 3.6 | pooled by SDS-PAGE/2nd use of CE | 64.4 | 0 | 5.1 |
| Q Sepharose FF | 8.0 (3CV 1M Tris pH 8.0 pre equil step) | 8.0 | 8.0 | 25 mM Tris pH 8.0 | 25 mM Tris, 90 mM NaCl, pH 8.0 | 20 | 20 | 3.6 | pooled by SDS-PAGE/3rd use of CE | 48.8 | 0 | 5.0 |
| Q Sepharose FF | 7.0 (3CV 1M Tris pH 8.0 pre equil step) | 8.0 | 7.0 | 25 mM Tris pH 8.0 | 25 mM Tris, 250 mM NaCl, pH 7.0 | 20 | 20 | 3.58 | pooled by SDS-PAGE/4th use of CE | 60.7 | 0 | 4.8 |
| Q Sepharose FF | 9.0 (3CV 1M Tris pH 8.0 pre equil step) | 9.0 | 9.0 | 25 mM Tris pH 8.0 | 25 mM Tris, 250 mM NaCl, pH 9.0 | 20 | 20 | 3.58 | pooled by SDS-PAGE/5th use of CE | 59.2 | 0 | 5.0 |
| Q Sepharose FF | 7.0 (3CV 1M Tris pH 7.0 pre equil step) | 7.0 | 7.0 | 25 mM Tris pH 7.0 | 25 mM Tris, 250 mM NaCl, pH 7.0 | 20 | 28 | 4.0 | bridged with SDS-page, pooled by CE pooling criteria evaluated <10% PEG-7 & <10% PEG-3 | 58.6 | 0 | 5.0 |
| Q Sepharose FF | 7.0 (3CV 1M Tris pH 7.0 pre equil step) | 7.0 | 7.0 | 25 mM Tris pH 7.0 | 25 mM Tris, 250 mM NaCl, pH 7.0 | 20 | 28 | 4.0 | pooled by CE criteria = 90% PEG-4 + 5 + 6 | 52.0 | 0 | 5.0 |
| Q Sepharose FF | 7.0 (3CV 1M Tris pH 7.0 pre equil step) | 7.0 | 7.0 | 25 mM Tris pH 7.0 | 25 mM Tris, 250 mM NaCl, pH 7.0 | 10 | 28 | 6.0 | pooled by CE criteria = 90% PEG-4 + 5 + 6 | 52.8 | 0 | 4.9 |
| Q Sepharose FF | 7.0 (3CV 1M Tris pH 7.0 pre equil step) | 7.0 | 7.0 | 25 mM Tris pH 7.0 | 25 mM Tris, 250 mM NaCl, pH 7.0 | 10 | 39 | 4.0 | theoretical pool by CE = 90% PEG-4 + 5 + 6 | 72.0 | 0 | 5.0 |
| Q Sepharose FF | 7.0 (3CV 1M Tris pH 7.0 pre equil step) | 7.0 | 7.0 | 25 mM Tris pH 7.0 | 25 mM Tris, 250 mM NaCl, pH 7.0 | 10 | 39 | 4.0 | CE of pool and pooling not completed | NA/ | N/A | N/A |

*= calculated based on CE analysis.

Example 2

Small Scale Procedure for Evaluation of the Effect of Additives on S-Sepharose FF Aggregation (Cation Exchange Chromatography Resin) of B-2036 PEG To a 15 ml centrifuge tube, 1.5 ml of S-Sepharose FF resin (settled bed volume) was added. The resin was prepared for protein binding by rinsing twice with 10 ml of a 1% solution of the additive to be evaluated in 25 mM Sodium acetate, pH 4. After each rinse, the supernatant was collected (by centrifuging) and decanted and discarded. To the rinsed resin pellet, 2.5 ml of 1% solution of the additive to be evaluated in 25 mM Sodium acetate, pH 4 was added and a quantity of UF/DF retentate was added containing approximately 5 mg of B-2036 PEG from step 3 (prepared by the method of flowchart 2, steps 1 through 3). The resin was then re-suspended in the solution and incubated with gentle mixing for 2 to 24 hrs. After incubation, the solution was centrifuged, and the supernatant decanted and discarded. The B-2036 PEG was then eluted from the resin by adding to the resin pellet 2.5 ml of a 1% solution of the additive to be evaluated in 25 mM Sodium acetate, pH 4 and 0.25 ml of 2.5M sodium chloride. The resin in the resulting solution was re-suspended and incubated with gentle mixing for 20 minutes. After incubation, the supernatant is retained by centrifuging, and decanted for analysis by size exclusion chromatography (e.g., SEHPLC (size exclusion HPLC). Then the used resin pellet is discarded. The above procedure was repeated for each additive to be evaluated using Cation Exchange Chromatography Resin to determine if aggregate formation could be eliminated or sufficiently decreased. Using this above-noted procedure, the results of Table 2 below were obtained. As reflected in Table 2, no additive tested using a cationic resin was as successful as was switching to anionic resin to decrease the level of aggregate formed.

Flowchart 2
Example 2
(Comparative Process Using Cation Exchange Resin)

| | UNIT OPERATION | PROCESS DESCRIPTION AND CONTROL | PROCESS CONTROLS |
|---|---|---|---|
| 1 | Pegylation | The B-2036 from the purified BI process is PEGylated with a 2 g/g excess of the PEGylation reagent, N-hydroxysuccinimidyl ester of methoxy(polyethylene glycol) propionic acid, MW 5,000 (m-SPA-5000) in 100 mM Hepes, pH 7.65. The PEGylated product is reacted in a stainless steel tank by the addition of solid PEG with stirring for 60-90 min.<br><br>=; pH = 7.65 in B-2036 UF/DF #2 buffer | API Step Range — Manf. Spec. — Demonstrated Acceptable<br><br>PEGylation<br>1. Temperature<br>  - low & high       18-25°C        15-28.9°C<br>2. pH<br>  - low & high       7.40-7.80      7.20-8.00<br>3. BI concentration  9.3 g/L        9-10 g/L |
| | ↓<br>Pegylated B-2036<br>↓ | | |
| 2 | Hydrophobic Interaction Chromatography (optional step) | The PEGylation reaction mixture is conditioned for hydrophobic interaction chromatography dilution (1:1) with 800 mM sodium citrate, 50 mM Tris, pH 7.6. The product is loaded onto the Phenyl column, washed with 400 mM sodium citrate, 50 mM Tris, pH 7.5, and product is collected by reverse salt gradient from 400 mM sodium citrate, 50 mM Tris, pH 7.5 to 50 mM Tris, pH 7.7 and fractions are collected when protein is detected by UV spectroscopy (e.g., the UV increases during elution).<br><br>Resin type: TosoHaas Toyopearl Phenyl 650M resin<br>Phenyl load: 1:1 of PEGylation pool with buffer<br>Flow rate: 60 cm/hr | Toyopearl Phenyl 650M<br>API Step Range — Manf. Spec. — Demonstrated Acceptable<br><br>1. Load capacity      </= 4.1 g/L resin   ≤ 5 g/L<br>2. Gradient slope     4+/-0.06 CV        3.88-4.12<br>3. Load conductivity  45-51 mS/cm        40-51 mS/cm<br><br>Column end equil conductivity            40-51 mS/cm<br><br>Final Load Conductivity 40-51 mS/cm<br>Peak Collection Start                    2 UV%<br>Pooling:       Bands observed between 36.5 – 200 kDa |

| Unit Operation | Process Description and Control | Process Controls |
|---|---|---|
| 2 (Cont.) (Hydrophobic Interaction Chromatography (optional step continued)) | Column Wash: ≥2 CV 50 mM Tris, 400 mM Sodium citrate, pH 7.5<br>Elution: 4CV gradient from 100% to 0% citrate<br><br>Pool fractions containing B-2036-PEG species following SDS-PAGE analysis of each fraction. | |
| | ↓ HIC Pool ↓ | |
| 3 Diafiltration (buffer exchange to cation exchanger buffer) | The protein pool solution from the Toyopearl Phenyl column is concentrated to 6 g/L concentration and diafiltered against 9 turnover volumes of 25 mM Sodium Acetate, pH 4.0 using a Millipore 10K MWCO Biomax membrane.<br><br>DF (diafiltration)<br>Buffer: 25 mM Na Acetate, pH 4.0<br><br>Transmembrane pressure (TMP): 20-25 psig<br><br>Total diafiltration volumes: 9 | UF/DF #3<br>API Step Range / Manf. Spec. / Demonstrated Acceptable<br><br>1. Final protein conc. 5.4-6.6 g/L </=7.2<br>2. TMP 20-25 psig<br>3. Retentate cross flow 20-25 LPM<br><br>End of WFI Rinses Conductivity ≤ 0.5 mS/cm<br>% Original NWP ≥ 60 %<br><br>Total g. B-2036 (Step Yield) ≥ 85 % |
| | ↓ Diafiltration Pool ↓ | |

| Unit Operation | Process Description and Control | Process Controls |
|---|---|---|
| 4. Cation Exchange Chromatography | Column chromatography using a cation exchange S Sepharose FF resin is performed using the final UF/DF#3 retentate. This step separates differentially PEGylated species into fractions for pooling to achieve the PEGylated species distribution required for API release. This column enriches for the PEG-4, PEG-5 and PEG-6 products of PEGylated BI (B-2036-PEG). The product is eluted with a linear gradient from 0-250 mM NaCl in 25 mM Sodium Acetate, pH 4.0 following equilibration steps and a 2 CV wash with 25 mM Sodium Acetate, pH 4.0. Pegvisomant is collected from the chromatography profile as a pool from fractions analyzed by SDS-PAGE with a pooling criteria of Pool primarily PEG-4 and PEG-5 species<br><br>Resin type: S Sepharose FF resin<br>Flow rate: 60 cm/hr Load, wash and elution<br>Equilibration: 25 mM Sodium Acetate, pH 4.0<br>Gradient: 20 CV linear gradient | Q-Sepharose FF<br>API Step — Manf. Spec. — Demonstrated Acceptable Range<br>1. Load/elute pH — 3.90-4.10<br>2. Load conductivity — ≤ 2.0 mS/cm<br>3. Load capacity — ≤ 4.0 g/L<br>Final Column Equil. PH — 4.0<br>Equil. Conductivity End — ≤ 2.0 mS/cm<br>Elution UV at Start of Collection — 2.5%<br>Pooling: Pool fractions of primarily PEG-4 & PEG-5 species |
| ↓ CEX Pool ↓ | | |
| 5. Diafiltration (buffer exchange to final API buffer) | The purpose of this step is to concentrate the pool of product from the S Sepharose FF column to 10 mg/L and perform a buffer exchange using 10K MWCO Biomax membranes into 18 g/L mannitol, 0.68 g/L glycine, 5 mM sodium phosphate, pH 7.4 through a total dialysis of 9 diavolumes. The material is then frozen as API. | UF/DF #4<br>1. Final protein conc. — 9.5-10.5 g/L — ≤ 15<br>2. TMP — 20-25 psig — 15-27.5<br>3. UF/DF Feed pressure — 20-35 psig<br>End of WFI Rinse Permeate Conductivity ≤ 0.5 mS/cm |

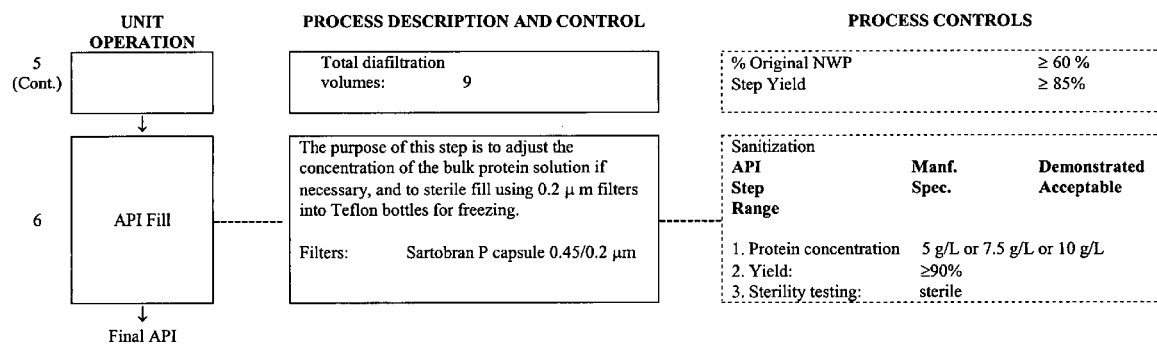

TABLE 2

(Results Obtained Using Cation Exchange Resin)
Small-Scale Procedure of Example 2

| Method | Resin loaded at 3.3 g/l |
|---|---|
| | 1.5 ml resin per trial |
| | Equilibrate resin with additive prior to protein load |
| | Elute by addition of 2.5 M NaCl/acetate pH 4, 1:10 v/v |
| | 24 hr incubation all 1% except as noted |

| Additive/Condition | % Aggregate |
|---|---|
| Control | 21.5 |
| 6M urea | 6.0 |
| CHAPS | 18.7 |
| Sarcosyl | 9.3 |
| PEG 3350 | 20.3 |
| Isopropanol | 19.3 |
| n propanol | 24.7 |
| n butanol | 27.1 |
| pH 7.7 50 mM TRIS control | 30.3 |
| | 32.2 overnight hold |
| 7.5 M urea | 10.7 |
| 6 M urea | 8.1 |
| 3 M urea | 32.3 |
| 1.5 M urea | 35.0 |
| tween 20 | 19.3 |
| methanol | 33.7 |
| ethanol | 33.5 |
| 5% sucrose | 31.6 |
| mannitol | 30.8 |
| 1% polyphosphate | 61.2 |
| 0.1% polyphosphate | 42.5 |
| 0.01% polyphosphate | 33.6 |
| 25 mm phosphate pH 2.2 | 19.7 |
| 25 mm phosphate pH 3 | 22.3 |
| 25 mm phosphate pH 5.5 | 63.1 |
| 25 mm phosphate pH 6.5 | 42.9 |
| 25 mm formate pH 4 | 29.0 |
| control 1 | 31.8 |
| control 2 | 31.1 |

Example 3

RPHPLC Analytical Technique RPHPLC is used here to monitor and quantitate percentages of pegylated species (e.g., PEG-4, PEG-5, and PEG-6) found in Q-Sepharose column fractions from anion exchange purification of pegvisomant.

25 uL of each Q-Sepharose (anion exchange step, see Example 1 above) fraction (protein concentrations ranging from 0.5 to 1.3 mg/mL) are applied to a Zorbax 300SB-CN column (4.6 mm×150 mm; 3.5 µm; Part Number 863973-905; serial number USMJ001205). Mobile phase A is 0.1% trifluoroacetic acid while mobile phase B consists of 0.085% trifluoroacetic acid in acetonitrile. A linear gradient from 40 to 50 percent Buffer B over 20 minutes at a flow rate of 1.0 mL/min at ambient temperature is used for separation of the different Pegylated forms of Pegvisomant. Absorbance is monitored at 214 nm.

The results obtained by RPHPLC are similar to those derived by capillary electrophoresis (CE) as indicated in FIGS. 2 4. below. Also, see Example 4 below for CE analytical technique exemplary procedure.

TABLE 3

Analysis of Q-Sepharose Fractions of Pegvisomant by Capillary Electrophoresis for Purposes of Determining the Percentages of Each PEGylated Species (fractions 7 through 18 were also analyzed by RPHPLC - see Table 4)

| fraction | starting concentration (mg/mL) | % PEG 2 | % PEG 3 | % PEG 4 | % PEG 5 | % PEG 6 | % PEG 7 | % PEG 8 |
|---|---|---|---|---|---|---|---|---|
| 2 | 0.59 | 0.0 | 0.0 | 2.8 | 26.3 | 39.6 | 25.3 | 6.0 |
| 3 | 0.88 | 0.0 | 0.0 | 4.6 | 28.6 | 44.8 | 18.8 | 3.2 |
| 4 | 1.04 | 0.0 | 0.0 | 5.8 | 28.1 | 48.6 | 15.9 | 1.7 |
| 5 | 1.16 | 0.0 | 0.0 | 6.2 | 28.3 | 49.8 | 14.1 | 1.6 |
| 6 | 1.23 | 0.0 | 0.0 | 5.4 | 29.9 | 54.5 | 10.2 | 0.0 |
| 7 | 1.27 | 0.0 | 0.0 | 5.2 | 33.0 | 54.1 | 7.7 | 0.0 |
| 8 | 1.27 | 0.0 | 0.0 | 5.3 | 40.3 | 50.6 | 4.8 | 0.0 |
| 9 | 1.25 | 0.0 | 0.0 | 4.5 | 49.9 | 41.8 | 3.8 | 0.0 |
| 10 | 1.24 | 0.0 | 0.0 | 5.1 | 59.5 | 33.1 | 2.3 | 0.0 |
| 11 | 1.21 | 0.0 | 0.0 | 6.2 | 65.9 | 25.4 | 2.5 | 0.0 |
| 12 | 1.17 | 0.0 | 0.0 | 7.9 | 74.4 | 17.7 | 0.0 | 0.0 |
| 13 | 1.13 | 0.0 | 0.0 | 15.3 | 72.6 | 12.2 | 0.0 | 0.0 |
| 14 | 1.09 | 0.0 | 0.0 | 21.4 | 70.7 | 8.0 | 0.0 | 0.0 |
| 15 | 1.05 | 0.0 | 0.0 | 37.3 | 57.3 | 5.4 | 0.0 | 0.0 |
| 16 | 1.01 | 0.0 | 0.0 | 48.2 | 47.0 | 4.8 | 0.0 | 0.0 |
| 17 | 0.97 | 0.0 | 0.0 | 55.8 | 40.2 | 3.9 | 0.0 | 0.0 |
| 18 | 0.91 | 0.0 | 2.1 | 62.4 | 31.8 | 3.6 | 0.0 | 0.0 |
| 19 | 0.84 | 0.0 | 0.0 | 80.8 | 19.2 | 0.0 | 0.0 | 0.0 |
| 20 | 0.77 | 0.0 | 1.2 | 78.2 | 20.7 | 0.0 | 0.0 | 0.0 |
| 21 | 0.71 | 0.0 | 6.8 | 77.3 | 15.9 | 0.0 | 0.0 | 0.0 |
| 22 | 0.65 | 0.0 | 12.3 | 75.9 | 11.9 | 0.0 | 0.0 | 0.0 |
| 23 | 0.61 | 0.0 | 18.9 | 70.3 | 10.8 | 0.0 | 0.0 | 0.0 |
| 24 | 0.56 | 0.0 | 21.5 | 69.5 | 9.0 | 0.0 | 0.0 | 0.0 |

The shaded region (i.e., fractions 7 through 18) represents fractions that were also analyzed by RPHPLC.

TABLE 4

Distribution of Different PEGylated Forms of Pegvisomant Across
Q-Sepharose Fractions As Determined By CE and RPHPLC

| fraction | % PEG-4 CE | % PEG-4 RP-HPLC | % PEG-5 CE | % PEG-5 RP-HPLC | % PEG-6 CE | % PEG-6 RP-HPLC | % PEG-7 CE | % PEG-7 RP-HPLC |
|---|---|---|---|---|---|---|---|---|
| 7 | 5.2 | 5.8 | 33.0 | 30.3 | 54.1 | 55.6 | 7.7 | 8.3 |
| 8 | 5.3 | 6.5 | 39.3 | 39.4 | 50.6 | 48.6 | 4.8 | 5.5 |
| 9 | 4.5 | 5.5 | 49.9 | 52.6 | 41.8 | 37.3 | 3.8 | 4.6 |
| 10 | 5.1 | 6.1 | 59.5 | 63.3 | 33.1 | 27.5 | 2.3 | 3.1 |
| 11 | 6.2 | 6.5 | 65.9 | 71.6 | 25.4 | 19.5 | 2.5 | 2.3 |
| 12 | 7.9 | 11.4 | 74.4 | 72.7 | 17.7 | 13.9 | 0.0 | 2.0 |
| 13 | 15.3 | 17.2 | 72.6 | 71.2 | 12.2 | 11.6 | 0.0 | 0.0 |
| 14 | 21.4 | 28.4 | 70.7 | 63.7 | 8.0 | 7.9 | 0.0 | 0.0 |
| 15 | 37.3 | 42.6 | 57.3 | 51.6 | 5.4 | 5.8 | 0.0 | 0.0 |
| 16 | 48.2 | 54.0 | 47.0 | 41.8 | 4.8 | 4.1 | 0.0 | 0.0 |
| 17 | 55.8 | 64.1 | 40.2 | 32.5 | 3.9 | 3.4 | 0.0 | 0.0 |
| 18 | 62.4 | 71.5 | 31.8 | 25.2 | 3.6 | 3.1 | 0.0 | 0.0 |

Comparative results of CE vs RPHPLC are depicted in Figures 2, 3 and 4 for B-2036 PEG 4, B-2036 PEG-5 and B-2036 PEG-6.

Example 4

CE Analytical Technique

Q-Sepharose fractions were analyzed by Capillary Electrophoresis as follows. The capillary, having a 50 µm Interior Diameter and effective length of 37 cm, was conditioned by rinsing with 1.0N NaOH for 10 minutes at 20 psi pressure followed by a 20 minute rinse with running buffer. The running buffer, 40 mM Phosphoric acid, 4 mg/mL O'O-Bis(2-aminopropyl) polyethylene glycol, 0.1 mg/mL polyethylene oxide, pH 1.9-2.0, was prepared from a 10× stock solution and filtered through a 0.22 µm filter in order to remove particulates that can cause clogs in the capillary.

Samples were warmed to room temperature in order to prevent aggregate formation when coming in contact with sample dilution buffer (40 mM Phosphoric acid, 4 mg/mL O'O-Bis(2-aminopropyl) polyethylene glycol, pH 1.9-2.2) or running buffer. Samples that were <0.5 mg/mL were not analyzed. Samples ≧0.5 mg/mL were injected neat while samples with a concentration >2.0 mg/mL were diluted to 2.0 mg/mL using sample dilution buffer. Samples were injected into the capillary using 0.5 psi pressure for 10 60 seconds. Following sample injection, run buffer was injected for 3 seconds at 0.5 psi in order to concentrate the sample. Samples were separated for 25 minutes at 30 kV at a minimum of 30° C. and detected at 214 nm. The capillary was rinsed prior to each subsequent sample injection with 0.1N NaOH for at least one minute at 20 psi and running buffer for two minutes in order to remove any retained sample from the capillary wall. Sample storage was held at 25-30° C.

The resulting electropherograms were integrated by splitting the peaks at the lowest point between neighboring peaks and the corrected area percent was calculated.

Using the above-noted procedure together with disclosure of Step 4, flowchart 1, Example 1, the results obtained by CE are those indicated in FIGS. 2-4 above.

Example 5

First Pooling Example

Q-Sepharose fractions were analyzed by CE as follows. The capillary, having a 50 µm interior diameter and effective length of 37 cm, was conditioned by rinsing with 1.0N NaOH for 10 minutes at 20 psi pressure followed by a 20 minute rinse with running buffer. The running buffer, 40 mM Phosphoric acid, 4 mg/mL O'O-Bis(2-aminopropyl) polyethylene glycol, 0.1 mg/mL polyethylene oxide, pH 1.9-2.0, was prepared from a 10X stock solution and filtered through a 0.22 µm filter in order to remove particulates that can cause clogs in the capillary.

Samples were warmed to room temperature in order to prevent aggregate formation when coming in contact with sample dilution buffer (40 mM Phosphoric acid, 4 mg/mL O'O-Bis(2-aminopropyl) polyethylene glycol, pH 1.9-2.2) or running buffer. Samples that were <0.5 mg/mL were not analyzed. Samples ≧0.5 mg/mL were injected neat while samples with a concentration >2.0 mg/mL were diluted to 2.0 mg/mL using sample dilution buffer. Samples were injected into the capillary using 0.5 psi pressure for 10 60 seconds. Following sample injection, running buffer was injected for 3 seconds at 0.5 psi in order to concentrate the sample. Samples were separated for 25 minutes at 30 kV at a minimum of 30° C. and detected at 214 nm. The capillary was rinsed prior to each subsequent sample injection with 0.1N NaOH for at least one minute at 20 psi and running buffer for two minutes in order to remove any retained sample from the capillary wall. Sample storage was held at 25-30° C.

The resulting electropherograms were integrated by splitting the peaks at the lowest point between neighboring peaks and the corrected area percent was calculated.

Using the above-noted procedure together with disclosure of Step 4, flowchart 1, Example 1, the results obtained by CE are those indicated in Table 5a below. A pool of enriched pegylated isoforms was prepared by using the criterion of accepting as a pool fractions, those fractions analyzed by CE with a composition of ≧74% PEG4+5+6 (first fraction) and >94% PEG4+5+6 (last fraction) and ≧0.5 mg/mL Fractions 6 through 25 (Table 5a below) were selected and combined into a pool using these criteria. The UF/DF#3 starting material and the combined pooled fractions were subjected to CE analysis as noted above. After selection and pooling of the fractions, the analysis of the pooled material shows enrichment of the PEG-4, PEG-5 and PEG-6 isoforms. See Table 5b indicating the same below.

TABLE 5a

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| 1 | 0.23 | | | | | | | | |
| 2 | 0.65 | | | | | | | | 0 |
| 3 | 0.91 | | | 2 | 18 | 40 | 32 | 9 | 60 |
| 4 | 1.06 | | | 3 | 19 | 41 | 31 | 6 | 63 |
| 5 | 1.15 | | | 4 | 22 | 43 | 27 | 5 | 69 |
| 6 | 1.21 | | | 4 | 26 | 44 | 23 | 3 | 74 |

TABLE 5a-continued

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| 7 | 1.27 | | | 3 | 28 | 49 | 20 | | 80 |
| 8 | 1.28 | | | 3 | 25 | 55 | 17 | | 83 |
| 9 | 1.28 | | | 3 | 25 | 60 | 12 | | 88 |
| 10 | 1.27 | | | 4 | 30 | 58 | 8 | | 92 |
| 11 | 1.25 | | | 4 | 47 | 43 | 6 | | 94 |
| 12 | 1.23 | | | 4 | 52 | 39 | 5 | | 95 |
| 13 | 1.20 | | | 3 | 62 | 31 | 4 | | 96 |
| 14 | 1.15 | | | 5 | 70 | 23 | 3 | | 98 |
| 15 | 1.11 | | | 6 | 69 | 24 | 1 | | 99 |
| 16 | 1.06 | | | 10 | 76 | 15 | | | 101 |
| 17 | 1.02 | | | 23 | 70 | 7 | | | 100 |
| 18 | 0.98 | | | 31 | 63 | 6 | | | 100 |
| 19 | 0.94 | | | 44 | 50 | 5 | | | 99 |
| 20 | 0.90 | | | 54 | 41 | 5 | | | 100 |
| 21 | 0.84 | | | 60 | 35 | 5 | | | 100 |
| 22 | 0.78 | | | 66 | 29 | 5 | | | 100 |
| 23 | 0.71 | | | 77 | 21 | 2 | | | 100 |
| 24 | 0.64 | | | 82 | 16 | 2 | | | 100 |
| 25 | 0.58 | | 2 | 83 | 13 | 2 | | | 98 |
| 26 | 0.54 | | 9 | 74 | 17 | 3 | | | 94 |
| 27 | 0.50 | | 18 | 68 | 14 | 0 | | | 82 |

TABLE 5b

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| UF/DF#3 pool | 5.86 | | 5 | 21 | 33 | 30 | 9 | 1 | 84 |
| Pooled Fractions | 1.04 | | | 25 | 38 | 30 | 7 | | 93 |

Example 6

Second Pooling Example

Q-Sepharose fractions were analyzed by CE as follows. The capillary, having a 50 μm interior diameter and effective length of 37 cm, was conditioned by rinsing with 1.0N NaOH for 10 minutes at 20 psi pressure followed by a 20 minute rinse with running buffer. The running buffer, 40 mM Phosphoric acid, 4 mg/mL O'O-Bis(2-aminopropyl) polyethylene glycol, 0.1 mg/mL polyethylene oxide, pH 1.9-2.0, was prepared from a 10x stock solution and filtered through a 0.22 μm filter in order to remove particulates that can cause clogs in the capillary.

Samples were warmed to room temperature in order to prevent aggregate formation when coming in contact with sample dilution buffer (40 mM Phosphoric acid, 4 mg/mL O'O-Bis(2-aminopropyl) polyethylene glycol, pH 1.9-2.2) or running buffer. Samples that were <0.5 mg/mL were not analyzed. Samples ≧0.5 mg/mL were injected neat while samples with a concentration >2.0 mg/mL were diluted to 2.0 mg/mL using sample dilution buffer. Samples were injected into the capillary using 0.5 psi pressure for 10 60 seconds. Following sample injection, running buffer was injected for 3 seconds at 0.5 psi in order to concentrate the sample. Samples were separated for 25 minutes at 30 kV at a minimum of 30° C. and detected at 214 nm. The capillary was rinsed prior to each subsequent sample injection with 0.1N NaOH for at least one minute at 20 psi and running buffer for two minutes in order to remove any retained sample from the capillary wall. Sample storage was held at 25-30° C.

The resulting electropherograms were integrated by splitting the peaks at the lowest point between neighboring peaks and the corrected area percent was calculated.

Using the above-noted procedure together with disclosure of Step 4, flowchart 1, Example 1, the results obtained by CE are those indicated in Table 6a below. A pool of enriched pegylated isoforms was prepared by using the criterion of accepting as a pool fractions, those fractions analyzed by CE with a composition of ≧75% PEG4+5+6 (first fraction) and ≧94% PEG4+5+6 (last fraction) and >0.5 mg/mL Fractions 3 through 20 (Table 6a below) were selected and combined into a pool using these criteria. The UF/DF#3 starting material (measured as HIC pool) and the combined pooled fractions were subjected to CE analysis as noted above. After selection and pooling of the fractions, the analysis of the pooled material shows enrichment of the PEG-4, PEG-5 and PEG-6 isoforms. See Table 6b indicating the same below.

TABLE 6a

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| 1 | 0.17 | | | | | | | | |
| 2 | 0.59 | | | 3 | 26 | 40 | 25 | 5 | 69 |

TABLE 6a-continued

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| 3 | 0.88 | | | 5 | 29 | 45 | 19 | 3 | 78 |
| 4 | 1.04 | | | 6 | 28 | 49 | 16 | 2 | 83 |
| 5 | 1.16 | | | 6 | 28 | 50 | 14 | | 98 |
| 6 | 1.24 | | | 5 | 30 | 55 | 10 | | 100 |
| 7 | 1.27 | | | 5 | 33 | 54 | 8 | | 100 |
| 8 | 1.27 | | | 5 | 39 | 51 | 5 | | 100 |
| 9 | 1.27 | | | 5 | 50 | 42 | 4 | | 100 |
| 10 | 1.24 | | | 5 | 60 | 33 | 2 | | 100 |
| 11 | 1.21 | | | 6 | 66 | 25 | 3 | | 100 |
| 12 | 1.17 | | | 8 | 74 | 18 | | | 100 |
| 13 | 1.13 | | | 15 | 73 | 12 | | | 100 |
| 14 | 1.09 | | | 21 | 71 | 8 | | | 100 |
| 15 | 1.05 | | | 37 | 57 | 5 | | | 100 |
| 16 | 1.01 | | | 48 | 47 | 5 | | | 100 |
| 17 | 0.97 | | | 56 | 40 | 4 | | | 100 |
| 18 | 0.91 | | 2 | 62 | 32 | 4 | | | 98 |
| 19 | 0.84 | | 0 | 81 | 19 | | | | 100 |
| 20 | 0.77 | | 1 | 78 | 21 | | | | 99 |
| 21 | 0.71 | | 7 | 77 | 16 | | | | 93 |
| 22 | 0.66 | | 12 | 76 | 12 | | | | 88 |
| 23 | 0.61 | | 19 | 70 | 11 | | | | 81 |
| 24 | 0.57 | | 22 | 70 | 9 | | | | 79 |

TABLE 6b

| Fraction # | Protein Conc. mg/ml | PEG-2 | PEG-3 | PEG-4 | PEG-5 | PEG-6 | PEG-7 | PEG-8 | PEG (4 + 5 + 6) |
|---|---|---|---|---|---|---|---|---|---|
| UF/DF#3 pool* | 3.51 | | 9 | 27 | 37 | 22 | 4 | | 86 |
| Pooled Fractions | 1.08 | | | 22 | 46 | 28 | 5 | | 96 |

*measured at HIC pool

While the prior description is provided with respect to recombinant B-2036 and recombinant B-2036 PEG, unless indicated otherwise, it is understood that the subject of the invention may be used with any recombinant pegylated growth hormone agonist, recombinant pegylated growth hormone antagonist, whether it be mammalian growth hormone or its antagonist, pegylated human growth hormone or its antagonist, or pegylated bovine growth hormone or its antagonist, any pegylated protein, any pegylated hormone, any pegylated antibody (or fragment(s)), etc.

What is claimed is:

1. A process for decreasing a level of aggregate of pegylated protein isoforms, wherein the pegylated protein is a growth hormone antagonist, said process comprising the steps of:
(a) providing said pegylated protein isoforms; and
(b) separating said pegylated protein isoforms by anion exchange chromatography using an anion exchange resin under sufficient conditions to decrease said level of said aggregate, wherein said level of said aggregate is less than 6% by weight based on the total weight of said isoforms and said aggregate, and wherein said pegylated protein isoforms comprises one or more of the isoforms PEG-1, PEG-2, PEG-3, PEG-4, PEG-5, PEG-6, PEG-7, PEG-8, and PEG-9 and any aggregate, trisulfide impurity and des-phe impurity thereof, and wherein said human growth hormone antagonist is B-2036.

2. The process of claim 1 further comprising the step of pegylating unpegylated or a partially pegylated form of the protein, or pegylating both to provide said pegylated protein isoforms.

3. The process of claim 2 wherein said pegylating step comprises pegylating with free PEG selected from the group consisting of PEG-N-hydroxysuccinimide-5K, PEG-succinimidyl carbonate-5K, PEG-succinimidyl-propionate-5K, PEG2-mailemide-40K (2×20K), PEG2-N-hydroxysuccimide-40K (2×20K), and PEG2-aldehyde-40K (2×20K).

4. The process of claim 3 wherein a stoichiometric weight ratio of said free PEG to said unpegylated protein is from about 0.5 to about 100.

5. The process of claim 4 wherein said stoichiometric weight ratio is from 1.5 to about 2.5.

6. The process of claim 2 wherein said pegylating step is conduced at pegylating pH from about 3 to about 10.

7. The process of claim 6 wherein said pegylated pH is from about 7.40 to about 7.80.

8. The process of claim 2 wherein said pegylation step is conducted at a pegylating temperature from about 18 to about 25° C.

9. The process of claim 1 further comprising an optional hydrophobic interaction chromatography (HIC) step of selecting said pegylated protein by HIC using an HIC resin.

10. The process of claim 2 further comprising an optional hydrophobic interaction chromatography (HIC) step selecting said pegylated protein by HIC using an HIC resin.

11. The process of claim 10 wherein said HIC load is less than or equal to about 4.1 g protein/L of packed bed-volume of HIC resin.

12. The process of claim 10 wherein said HIC step is conducted at HIC temperature from about 10 to about 40° C.

13. The process of claim 10 further comprising a ultrafiltering/diafiltering (UF/DF#3) step, ultrafiltering/diafiltering (UF/DF#3) of an eluent from said HIC step.

14. The process of claim 1 wherein said step (b) further comprises a step of loading said pegylated protein including any impurity and any aggregate thereof on said anion exchange (AEX) resin to provide loaded pegylated protein.

15. The process of claim 14 wherein the loading step is conducted at an AEX loading conductivity of less than or equal to about 10 mS/cm.

16. The process of claim 14 wherein the loading step is conducted at a loading pH from about 5 to about 10.

17. The process of claim 14 wherein the loading step is conducted at an AEX load of pegylated protein including any impurity or said aggregate thereof of less than or equal to about 10 g protein/L of packed bed-volume of AEX resin.

18. The process of claim 1 further comprising a pooling step (c) of pooling discrete amounts of said pegylated protein isoforms to yield a pooled pegylated protein by/a technique selected from the group consisting of capillary electrophoresis (CE), sodium dodeCyl sulfate-polyacrylamide gel electrophoresis (SDS-PAGE), hydrophobic interaction chromatography (HIC), anion exchange (AEX) chromatography, cation exchange (CEX) chromatography, reverse-phase high pressure liquid chromatography (RPHPLC), size exclusion high pressure liquid chromatography (SEHPLC), affinity chromatography (AC) and combinations thereof.

19. A process for decreasing a level of aggregate of pegylated protein isoforms, wherein the pegylated protein is a growth hormone antagonist, said process comprising the steps of:
(a) providing said pegylated protein isoforms; and
(b) separating said pegylated protein isoforms by anion exchange chromatography using an anion exchange resin under sufficient conditions to decrease said level of said aggregate, wherein said level of said aggregate is less than 6% by weight based on the total weight of said isoforms and said aggregate, and wherein said human growth hormone antagonist is B-2036.

20. The process of claim 19 wherein said human growth hormone antagonist comprises an amino acid sequence of SEQ ID NO:1.

21. The process of claim 1 wherein said human growth hormone antagonist comprises an amino acid sequence of SEQ ID NO:1.

22. The process of claim 18 wherein said pooled pegylated protein comprises isoforms PEG-4, PEG-5, and PEG-6.

23. The process of claim 18 wherein said pooled pegylated protein comprises at least 90% by weight based on a total weight of PEG-1, PEG-2, PEG-3, PEG-4, PEG-5, PEG-6, PEG-7, PEG-8 and PEG-9 pegylated protein isoforms and any aggregate thereof.

24. The process of claim 18 wherein said pooled pegylated protein comprises at least 94% by weight based on a total weight of PEG-1, PEG-2, PEG-3, PEG-4, PEG-5, PEG-6, PEG-7, PEG-8 and PEG-9 pegylated protein isoforms and any aggregate thereof.

25. The process of claim 18 wherein said pooled pegylated protein consists essentially of isoforms PEG-3, PEG-4, PEG-5, PEG-6, and PEG-7.

26. The process of claim 18 wherein said pooled pegylated protein consists essentially of isoforms PEG-4, PEG-5, and PEG-6.

27. The process of claim 1 wherein said level of aggregate is less than or equal to about 5% by weight of the pegylated protein.

28. The process of claim 1 wherein said level of aggregate is less than or equal to about 2% by weight of the pegylated protein.

* * * * *